United States Patent
Baum et al.

(10) Patent No.: US 7,741,115 B2
(45) Date of Patent: Jun. 22, 2010

(54) ANTIBODIES THAT BIND LDCAM

(75) Inventors: Peter Robert Baum, Seattle, WA (US); William Christian Fanslow, III, Normandy Park, WA (US)

(73) Assignee: Immunex Corporation, Thousand Oaks, CA (US)

( * ) Notice: Subject to any disclaimer, the term of this patent is extended or adjusted under 35 U.S.C. 154(b) by 0 days.

(21) Appl. No.: 12/218,654

(22) Filed: Jul. 16, 2008

(65) Prior Publication Data

US 2009/0011499 A1 Jan. 8, 2009

Related U.S. Application Data

(63) Continuation of application No. 10/622,237, filed on Jul. 17, 2003, now abandoned, which is a continuation of application No. 09/778,187, filed on Feb. 6, 2001, now Pat. No. 7,402,655, which is a continuation-in-part of application No. PCT/US99/17905, filed on Aug. 5, 1999.

(60) Provisional application No. 60/095,672, filed on Aug. 7, 1998.

(51) Int. Cl.
*C12N 5/20* (2006.01)
*C07K 16/24* (2006.01)

(52) U.S. Cl. .................... 435/326; 530/388.23

(58) Field of Classification Search .............. None
See application file for complete search history.

(56) References Cited

U.S. PATENT DOCUMENTS

| 6,512,095 B2 | 1/2003 | Baum |
| 6,642,360 B2 | 11/2003 | Filvaroff et al. |
| 7,402,655 B2 * | 7/2008 | Baum et al. ............. 530/350 |
| 2002/0198147 A1 | 12/2002 | Baker et al. |

FOREIGN PATENT DOCUMENTS

| WO | WO99/28462 | 6/1999 |
| WO | WO99/57132 | 11/1999 |
| WO | WO00/29435 | 5/2000 |
| WO | WO00/32776 | 6/2000 |
| WO | WO01/00237 A1 | 1/2001 |
| WO | WO01/54477 A2 | 8/2001 |
| WO | WO02/26930 A2 | 4/2002 |

OTHER PUBLICATIONS

Attwood, T. "The bable of bioinformatics," *Science*, 290:47-49, 2000.
Bost, K.L. And Pascual, D.W., "Antibodies against a peptide sequence within the HIV envelope protein crossreacts with human interleukin-2," *Immunol. Invest.*, 17(6-7):577-586, 1988.
Gomyo, H. et al., "A 2-Mb sequence-ready contig map and a novel immunoglobulin superfamily gene *IGSF4* in the LOH region of chromosome 11q23.2," *Genomics*, 62:139-146, 1999.
Greene, J.L. et al., "Covalent dimerization of CD28/CTLA-4 and oligomerization of CD80/CD86 regulate T cells costimulatory interactions," *J. Biol. Chem.*, 271(43):26762-26771, 1996.
Linsley, P.S. et al., "Binding stoichiometry of the cytotoxic T lymphocyte-associated molecule-4 (CTLA-4)," *J. Biol. Chem.*, 270(25):15417-15424, 1995.
Metzler et al., "Solution structure of human CLTA-4 and delineation of a CD80/CD86 binding site conserved in CD28," *Nat. Struct. Biol.*, 4:527-531, 1997.
Skolnick et al. "From genes to protein structure and function: novel applications of computational approaches in the genomic era," *Trends in Biotech.*, 18(1):34-39, 2000.
Strausberg, R., Genebank, Accession No. AA493561, Aug. 28, 1997.
The RIKEN Genome Exploration Research Group Phase II Team and the FANTOM Consortium; "Functional annotation of a full-length mouse cDNA collection," *Nature* 409:685-690, 2001.
Urase K., et al., Expression of TRA175 mRNA, a new member of the immunoglobulin superfamily, in developing mouse brain, *NeuroReport* 12(15):3217-3221, Oct. 2001.
Wakayama T., et al., "Cloning and Characterization of a Novel Mouse Immunoglobulin Superfamily Gene Expressed in Early Spermatogenic Cells," *Molecular Reproduction and Development* 60:158-164, 2001.

* cited by examiner

*Primary Examiner*—Maher M Haddad
(74) *Attorney, Agent, or Firm*—James E. Klaniecki

(57) ABSTRACT

The invention is directed to LDCAM as a purified and isolated protein, the DNA encoding the LDCAM, host cells transfected with cDNAs encoding LDCAM, processes for preparing LDCAM polypeptides and compositions and methods for treating utilizing LDCAM polypeptides.

5 Claims, No Drawings

ANTIBODIES THAT BIND LDCAM

CROSS-REFERENCE TO RELATED APPLICATIONS

This application is a continuation of U.S. patent application Ser. No. 10/622,237, filed Jul. 17, 2003 now abandoned, which is a continuation of U.S. patent application Ser. No. 09/778,187, filed Feb. 6, 2001 now U.S. Pat. No. 7,402,655, which is a continuation-in-part of International Application No. PCT/US99/17905, filed 5 Aug. 1999, which was published under PCT Article 21(2) on 17 Feb. 2000, in English, as WO 00/08158, and which claims the benefit of U.S. Provisional Application Ser. No. 60/095,672, filed 07 Aug. 1998, all of which are incorporated herein by reference.

BACKGROUND

1. Field of the Invention

The present invention relates to new molecules, designated LDCAM, capable of modulating or altering T cell function. More particularly, the present invention involves novel polypeptides that interact with T cell surface molecules to alter signaling, bind to themselves and bind to another novel polypeptide, designated B7L-1, and generate increases in natural killer cell populations. The invention includes LDCAM molecules, DNA encoding LDCAM molecules, processes for production of recombinant LDCAM polypeptides, and pharmaceutical compositions containing such LDCAM polypeptides.

2. Description of Related Art

Adhesion molecules play important roles in cell signaling within the immune system and other cellular systems. In addition to the antigen specific signals delivered by the T cell receptor complex, the shape and type of immune response by T cells depend upon costimulatory signals mediated by adhesion molecules on antigen presenting cells (APC). One such costimulatory signaling involves the adhesion molecules B7-1 (CD80) and B7-2 (CD86) which send important signals through their T cell surface receptors, CD28 and CTLA4 (CD152). B7-1 interacts with CD28 to signal cytokine production, cell proliferation, and the generation of effector and memory T cells. If the signal through CD28 is blocked, T cell anergy or immune deviation can occur, resulting in severely depressed or altered immune responses.

B7-1 also interacts with the T cell CTLA4 receptor. Its signaling is complex, but one component provides a negative feedback signal, causing the T cell to attenuate the CD28 signal. In the absence of this signal, rampant T cell proliferation and effector cell activation continues. When this feedback regulation malfunctions, autoimmune diseases and lymphoproliferation can result. For example, when the CD28 and B7-1 (and B7-2) interaction is blocked with an anti-CTLA4 antibody, increased tumor immunity and lymphoproliferation have been observed.

B7-2, which is expressed on different cells and at different stages of APC activation from that of B7-1, also delivers its costimulatory signal to T cells through CD28 and CTLA4. The B7-2 signal can lead to immune responses that are identical to, or different from the immune responses resulting from B7-1 signaling. The nature of the B7-2 signaling depends upon the cellular context and the timing of the costimulation.

Even though they bind to the same cellular receptors, B7-1 and B7-2 are only weakly related at the amino acid level. Both, however, are members of the extended immunoglobulin domain containing superfamily and much of their shared sequence homology is due to the particular residues shared by their common Ig domains, which are characteristic of the Ig-domain subfamily.

There is evidence to suggest that other adhesion molecules are important in T cell response to antigens. For example, T cell proliferation and cytokine production that occurs in response to engagement of a T cell receptor by an antigen can occur in the absence of CD28 in certain diseases. Proliferation and cytokine production also occurs in the absence of CD28 in memory responses, and in systems in which CD28 has been genetically removed. In some cases, T cell proliferation depends upon an interaction within the CD48 or the ICAM/LFA systems. Furthermore, the adhesion molecule known as ALCAM interacts with its T cell ligand CD6 to modulate the CD3 signal.

Clearly, signaling through T cell surface receptors plays an important role in maintaining balance in the immune system. Systems with a predominance of activatory signals, such as the costimulatory signaling between CD28 and B7-1, can lead to autoimmunity and inflammation. Immune systems with a predominance of inhibitory signals, such as the costimulatory signaling between CTLA4 and are less able to challenge infected cells or cancer cells. Isolating new molecules involved in T cell signaling is highly desirable for studying the biological signal(s) transduced via their receptors. Additionally, identifying such molecules provides a means of regulating and treating diseased states associated with autoimmunity, inflammation and infection.

SUMMARY OF THE INVENTION

The present invention provides mammalian polypeptides, designated LDCAM, so designated because they are found on lymphoid derived dendritic cells and display a limited homology to adhesion molecules, including B7-1. The LDCAM molecules described herein include isolated or homogeneous proteins that bind to themselves, have limited homology with B7L-1 (described in copending application Ser. No. 60/095,663 filed Aug. 7, 1998 (incorporated herein by reference) and for which B7-L1 is a binding protein. The present invention further includes isolated DNAs encoding LDCAM and expression vectors comprising DNA encoding mammalian LDCAM. Within the scope of this invention are host cells that have been transfected or transformed with expression vectors that comprise a DNA encoding LDCAM, and processes for producing LDCAM by culturing such host cells under conditions conducive to expression of LDCAM. Further within the present invention are pharmaceutical compositions comprising soluble forms of LDCAM molecules and methods for modulating T cell immune responses by administering the pharmaceutical compositions. Additional methods encompassed by the present invention include generating natural killer cells by administering pharmaceutical compositions to an individuals or by combining LDCAM and natural killer cell precursor cells ex vivo.

DETAILED DESCRIPTION OF THE INVENTION

Novel proteins designated LDCAM are provided herein. Further provided are DNA encoding LDCAM, recombinant expression vectors comprising LDCAM, and methods for producing recombinant LDCAM polypeptides that include cultivating host cells transformed with an expression vector under conditions appropriate for expressing LDCAM and recovering the expressed LDCAM.

B7L-1, a molecule having sequence similarity to B7-1, described in copending application Ser. No. 60/095,663 filed Aug. 7, 1998, is a binding protein for the LDCAM polypeptides of the present invention. Because B7L-1 is a LDCAM binding protein and because B7L-1 and LDCAM display homology within their intracellular domain that includes potential binding sites for band 4.1 and PDZ family members, and are found on many of the same cell types, their cell bound forms may deliver similar signals when engaged. Thus, they are termed co-receptors or counterstructures. The nucleotide sequence encoding long and short extracellular forms of human B7L-1 are presented in SEQ ID NO:7 and SEQ ID NO:9, respectively. The amino acid sequences encoded by the nucleotide sequences of SEQ ID NO:7 and SEQ ID NO:9 are disclosed in SEQ ID NO:8 and SEQ ID NO:10, respectively.

To identify cell lines to which B7L-1 binds and to subsequently isolate a protein to which B7L-1 binds, a B7L-1/Fc fusion protein was prepared as described in Example 1 and binding studies, described in Example 2, were carried out. Example 3 describes screening a cDNA library prepared from WI-26, a cell line to which B7L-1 binds, and identifying a full length LDCAM human clone. The nucleotide sequence encoding human LDCAM, isolated as described in Example 3, is presented in SEQ ID NO:1, and the amino acid sequence encoded thereby is presented in SEQ ID NO:2. The encoded human LDCAM amino acid sequence described in SEQ ID NO:2 has a predicted extracellular domain of 374 amino acids including a leader sequence of 38 amino acids 1-38; a transmembrane domain of 21 amino acids (375-395) and a cytoplasmic domain of 47 amino acids (396-442).

Examples 5 and 6 describe making and using a human LDCAM/Fc in binding studies to identify cell lines to which the human LDCAM binds. Among cell lines positively identified were S49.1 cells and lymphoid dendritic cells from spleens and lymph nodes of Flt3-L treated mice. Example 7 describes screening pools of an expression library to identify murine LDCAM clones. The isolated murine LDCAM DNA sequence is disclosed in SEQ ID NO:3. The amino acid sequence encoded by the nucleotide sequence of SEQ ID NO:3 is disclosed in SEQ ID NO:4. The encoded murine LDCAM amino acid sequence (SEQ ID NO:4) has a predicted extracellular domain of 356 amino acids (residues 1-356); a transmembrane domain of 21 amino acids (357-377); and a cytoplasmic domain that includes amino acid residues 378-423. SEQ ID NO:3 and SEQ ID NO:4 describes the full length mature murine LDCAM sequences. As compared to the human LDCAM sequence, the signal sequence is not completely described.

The purified mammalian LDCAM molecules described herein are Type I transmembrane proteins having limited overall homology to B7-1 and other cell adhesion molecules. LDCAM has high homology to the cytoplasmic region of B7L-1. As described below in Example 6, LDCAM proteins demonstrate widespread expression. In particular, human LDCAM mRNA is found in breast, retina, fetal liver spleen, fetal heart, lung, muscle, placenta, thyroid, and lung carcinoma. Cell lines that have LDCAM message include Wi-26. Mouse LDCAM mRNA is found on whole embryo, testes, triple negative cells murine splenic and lymph node $CD8^+$, S49.1 and dendritic cells.

The discovery of the DNA sequences disclosed in SEQ ID NOs:1 and 3 enables construction of expression vectors comprising DNAs encoding human and mouse LDCAM proteins; host cells transfected or transformed with the expression vectors; biologically active LDCAM as homogeneous proteins; and antibodies immunoreactive with LDCAM.

Like B7L-1, LDCAM has limited homology to poliovirus receptor, delta opoid binding protein and adhesion molecules. Moreover, as described in Example 13, LDCAM blocks T cell proliferation caused by ConA and PHA, suggesting the LDAM is useful in modulating T cell mediated immune response. LDCAM does not inhibit TCR mAb induced T cell proliferation suggesting that the inhibitory effects of LDCAM on mitogen-induced T cell proliferation is due to inhibition of cytokine secretion, e.g. IL-2, or due to the regulation of downstream responses of the T cell following activation and increases in the expression of the LDCAM binding partner. While not limited to such, particular uses of the LDCAM molecules are described infra.

As used herein, the term LDCAM encompasses polypeptides having the amino acid sequence 1-442 of SEQ ID NO:2 and the amino acid sequence 1-423 of SEQ ID NO:4. In addition, LDCAM encompasses polypeptides that have a high degree of similarity or a high degree of identity with the amino acid sequence of SEQ ID NO:2, the amino acid sequence of SEQ ID NO:4, and which polypeptides are biologically active. The term "LDCAM" refers to a genus of polypeptides that bind and complex with themselves, polypeptides for which B7L-1 is a binding protein, and polypeptides that alter T cell signals in response to antigen and mitogens The term "murine LDCAM" refers to biologically active gene products of the DNA of SEQ ID NO:3 and the term "human LDCAM" refers to biologically active gene products of the DNA of SEQ ID NO:1. Further encompassed by the term "LDCAM" are soluble or truncated proteins that comprise primarily the B7L-1 co-binding portion of the protein, retain biological activity and are capable of being secreted. Specific examples of such soluble proteins are those comprising the sequence of amino acids 1-374 of SEQ ID NO:2 and those comprising the sequence of amino acids 1-356 of SEQ ID NO:4. Alternatively, such soluble proteins can exclude a leader sequence and thus encompass amino acids 39-374 of SEQ ID NO:2.

The term "biologically active" as it refers to LDCAM, means that the LDCAM is capable of altering T cell signals in response to mitogens.

"Isolated" means that LDCAM is free of association with other proteins or polypeptides, for example, as a purification product of recombinant host cell culture or as a purified extract.

A "LDCAM variant" as referred to herein, means a polypeptide substantially homologous to native LDCAM, but which has an amino acid sequence different from that of native LDCAM (human, murine or other mammalian species) because of one or more deletions, insertions or substitutions. The variant amino acid sequence preferably is at least 80% identical to a native LDCAM amino acid sequence, most preferably at least 90% identical. The percent identity may be determined, for example, by comparing sequence information using the GAP computer program, version 6.0 described by Devereux et al. (*Nucl. Acids Res.* 12:387, 1984) and available from the University of Wisconsin Genetics Computer Group (UWGCG). The preferred default parameters for the GAP program include: (1) a unary comparison matrix (containing a value of 1 for identities and 0 for non-identities) for nucleotides, and the weighted comparison matrix of Gribskov and Burgess, *Nucl. Acids Res.* 14:6745, 1986, as described by Schwartz and Dayhoff, eds., *Atlas of Protein Sequence and Structure*, National Biomedical Research Foundation, pp. 353-358, 1979; (2) a penalty of 3.0 for each gap and an additional 0.10 penalty for each symbol in each gap; and (3) no penalty for end gaps. Variants may comprise conservatively substituted sequences, meaning that a given amino acid residue is replaced by a residue having similar physiochemical characteristics. Examples of conservative substitutions include substitution of one aliphatic residue for another, such as Ile, Val, Leu, or Ala for one another, or substitutions of one polar residue for another, such as between Lys and Arg; Glu and Asp; or Gln and Asn. Other such conservative substitutions, for example, substitutions of entire regions having similar hydrophobicity characteristics, are well known. Naturally occurring LDCAM variants or alleles are also encompassed by the invention. Examples of such variants are proteins that result from alternate mRNA splicing events or from proteolytic cleavage of the LDCAM protein, wherein the LDCAM binding property is retained. Alternate splicing of mRNA may yield a truncated but biologically active LDCAM protein, such as a naturally occurring soluble form of the protein, for example. Variations attributable to proteolysis include, for example, differences in the N- or C-termini upon expression in different types of host cells, due to proteolytic removal of one or more terminal amino acids from the LDCAM protein (generally from 1-5 terminal amino acids).

Example 9 describes the construction of a novel LDCAM/Fc fusion protein that may be utilized in LDCAM binding studies and studies directed to examining functional characteristics of the molecule. Other antibody Fc regions may be substituted for the human IgG1 Fc region described in the Example. Other suitable Fc regions are those that can bind with high affinity to protein A or protein G, or those that include fragments of the human or murine IgG1 Fc region, e.g., fragments comprising at least the hinge region so that interchain disulfide bonds will form. The LDCAM fusion protein offers the advantage of being easily purified. In addition, disulfide bonds form between the Fc regions of two separate fusion protein chains, creating dimers.

As described supra, an aspect of the invention is soluble LDCAM polypeptides. Soluble LDCAM polypeptides comprise all or part of the extracellular domain of a native LDCAM but lack the signal that would cause retention of the polypeptide on a cell membrane. Soluble LDCAM polypeptides advantageously comprise the native (or a heterologous) signal peptide when initially synthesized to promote secretion, but the signal peptide is cleaved upon secretion of LDCAM from the cell. Soluble LDCAM polypeptides encompassed by the invention retain the ability to bind B7L-1, or the ability to bind to themselves. Alternatively soluble LDCAM polypeptides of the present invention retain the ability to alter T cell responses. Soluble LDCAM may include part of the signal or part of the cytoplasmic domain or other sequences, provided that the soluble LDCAM protein can be secreted.

Soluble LDCAM may be identified (and distinguished from its non-soluble membrane-bound counterparts) by separating intact cells which express the desired protein from the culture medium, e.g., by centrifugation, and assaying the medium or supernatant for the presence of the desired protein. The presence of LDCAM in the medium indicates that the protein was secreted from the cells and thus is a soluble form of the desired protein.

Soluble forms of LDCAM possess many advantages over the native bound LDCAM protein. Purification of the proteins from recombinant host cells is feasible, since the soluble proteins are secreted from the cells. Further, soluble proteins are generally more suitable for intravenous administration.

Examples of soluble LDCAM polypeptides include those comprising a substantial portion of the extracellular domain of a native LDCAM protein. For example, a soluble human LDCAM protein comprises amino acids 38-374 or 1-374 of SEQ ID NO:2 and a soluble murine LDCAM includes amino acids 1-356 of SEQ ID NO:4. In addition, truncated soluble LDCAM proteins comprising less than the entire extracellular domain are included in the invention. When initially expressed within a host cell, soluble LDCAM may include one of the heterologous signal peptides described below that is functional within the host cells employed. Alternatively, the protein may comprise the native signal peptide. In one embodiment of the invention, soluble LDCAM can be expressed as a fusion protein comprising (from N- to C-terminus) the yeast α-factor signal peptide, a FLAG® peptide described below and in U.S. Pat. No. 5,011,912, and soluble LDCAM consisting of amino acids 39-374 of SEQ ID NO:2 or 21-356 of SEQ ID NO:4. This recombinant fusion protein is expressed in and secreted from yeast cells. The FLAG® peptide facilitates purification of the protein, and subsequently may be cleaved from the soluble LDCAM using bovine mucosal enterokinase. Isolated DNA sequences encoding soluble LDCAM proteins are encompassed by the invention.

Truncated LDCAM, including soluble polypeptides, may be prepared by any of a number of conventional techniques. A desired DNA sequence may be chemically synthesized using techniques known per se. DNA fragments also may be produced by restriction endonuclease digestion of a full length cloned DNA sequence, and isolated by electrophoresis on agarose gels. Linkers containing restriction endonuclease cleavage site(s) may be employed to insert the desired DNA fragment into an expression vector, or the fragment may be digested at cleavage sites naturally present therein. The well known polymerase chain reaction procedure also may be employed to amplify a DNA sequence encoding a desired protein fragment. As a further alternative, known mutagenesis techniques may be employed to insert a stop codon at a desired point, e.g., immediately downstream of the codon for the last amino acid of the receptor-binding domain.

As stated above, the invention provides isolated or homogeneous LDCAM polypeptides, both recombinant and non-recombinant. Additionally within the scope of the present invention are variants and derivatives of native LDCAM proteins that retain the desired biological activity. Such activity includes the ability of LDCAM to bind to itself, or the ability to bind to B7L-1, or the ability to alter T cell signaling. LDCAM variants and derivatives may be obtained by mutations of nucleotide sequences coding for native LDCAM polypeptides. Alterations of the native amino acid sequence may be accomplished by any of a number of conventional methods. Mutations can be introduced at particular loci by synthesizing oligonucleotides containing a mutant sequence, flanked by restriction sites enabling ligation to fragments of the native sequence. Following ligation, the resulting reconstructed sequence encodes an analog having the desired amino acid insertion, substitution, or deletion.

Alternatively, oligonucleotide-directed site-specific mutagenesis procedures can be employed to provide an altered gene wherein predetermined codons can be altered by substitution, deletion or insertion. Exemplary methods of making the alterations set forth above are disclosed by Walder et al. (*Gene* 42:133, 1986); Bauer et al. (*Gene* 37:73, 1985); Craik (*BioTechniques*, January 1985, 12-19); Smith et al. (*Genetic Engineering: Principles and Methods*, Plenum Press, 1981); Kunkel (*Proc. Natl. Acad. Sci. USA* 82:488, 1985); Kunkel et al. (*Methods in Enzymol.* 154:367, 1987); and U.S. Pat. Nos. 4,518,584 and 4,737,462 all of which are incorporated by reference.

LDCAM may be modified to create LDCAM derivatives by forming covalent or aggregative conjugates with other chemical moieties, such as glycosyl groups, lipids, phosphate, acetyl groups and the like. Covalent derivatives of LDCAM may be prepared by linking the chemical moieties to functional groups on LDCAM amino acid side chains or at the N-terminus or C-terminus of a LDCAM polypeptide or the extracellular domain thereof. Other derivatives of LDCAM within the scope of this invention include covalent or aggregative conjugates of LDCAM or its fragments with other proteins or polypeptides, such as by synthesis in recombinant culture as N-terminal or C-terminal fusions. For example, the conjugate may comprise a signal or leader polypeptide sequence (e.g. the α-factor leader of Saccharomyces) at the N-terminus of a LDCAM polypeptide. The signal or leader peptide co-translationally or post-translationally directs transfer of the conjugate from its site of synthesis to a site inside or outside of the cell membrane or cell wall.

LDCAM polypeptide fusions can comprise peptides added to facilitate purification and identification of LDCAM. Such peptides include, for example, poly-His or the antigenic identification peptides described in U.S. Pat. No. 5,011,912 and in Hopp et al., Bio/Technology 6:1204, 1988.

The invention further includes LDCAM polypeptides with or without associated native-pattern glycosylation. LDCAM expressed in yeast or mammalian expression systems (e.g., COS-7 cells) may be similar to or significantly different from a native LDCAM polypeptide in molecular weight and glycosylation pattern, depending upon the choice of expression system. Expression of LDCAM polypeptides in bacterial expression systems, such as E. coli, provides non-glycosylated molecules.

Equivalent DNA constructs that encode various additions or substitutions of amino acid residues or sequences, or deletions of terminal or internal residues or sequences not needed for biological activity or binding are encompassed by the invention. For example, N-glycosylation sites in the LDCAM extracellular domain can be modified to preclude glycosylation, allowing expression of a reduced carbohydrate analog in mammalian and yeast expression systems. N-glycosylation sites in eukaryotic polypeptides are characterized by an amino acid triplet Asn-X-Y, wherein X is any amino acid except Pro and Y is Ser or Thr. The human LDCAM polypeptide of SEQ ID NO:2 includes six such triplets, at amino acids 67-69, 101-103, 113-115, 165-167, 304-306, and 308-310. Similarly, the murine LDCAM polypeptide of SEQ ID NO:4 includes sic such triplets at 49-51, 83-85, 95-97, 147-149, 286-288 and 290-292. Appropriate substitutions, additions or deletions to the nucleotide sequence encoding these triplets will result in prevention of attachment of carbohydrate residues at the Asn side chain. Alteration of a single nucleotide, chosen so that Asn is replaced by a different amino acid, for example, is sufficient to inactivate an N-glycosylation site. Known procedures for inactivating N-glycosylation sites in proteins include those described in U.S. Pat. No. 5,071,972 and EP 276,846, hereby incorporated by reference.

In another example, sequences encoding Cys residues that are not essential for biological activity can be altered to cause the Cys residues to be deleted or replaced with other amino acids, preventing formation of incorrect intramolecular disulfide bridges upon renaturation. Other equivalents are prepared by modification of adjacent dibasic amino acid residues to enhance expression in yeast systems in which KEX2 protease activity is present. EP 212,914 discloses the use of site-specific mutagenesis to inactivate KEX2 protease processing sites in a protein. KEX2 protease processing sites are inactivated by deleting, adding or substituting residues to alter Arg-Arg, Arg-Lys, and Lys-Arg pairs to eliminate the occurrence of these adjacent basic residues. Lys-Lys pairings are considerably less susceptible to KEX2 cleavage, and conversion of Arg-Lys or Lys-Arg to Lys-Lys represents a conservative and preferred approach to inactivating KEX2 sites.

Nucleic acid sequences within the scope of the invention include isolated DNA and RNA sequences that hybridize to the LDCAM nucleotide sequences disclosed herein under conditions of moderate or severe stringency, and that encode biologically active LDCAM. Conditions of moderate stringency, as defined by Sambrook et al. Molecular Cloning: A Laboratory Manual, 2 ed. Vol. 1, pp. 101-104, Cold Spring Harbor Laboratory Press, (1989), include use of a prewashing solution of 5×SSC, 0.5% SDS, 1.0 mM EDTA (pH 8.0) and hybridization conditions of about 55° C., 5×SSC, overnight. Conditions of severe stringency include higher temperatures of hybridization and washing. The skilled artisan will recognize that the temperature and wash solution salt concentration may be adjusted as necessary according to factors such as the length of the nucleic acid molecule.

Due to the known degeneracy of the genetic code wherein more than one codon can encode the same amino acid, a DNA sequence may vary from that shown in SEQ ID NO:1 and 3 and still encode a LDCAM protein having the amino acid sequence of SEQ ID NO:2 and SEQ ID NO:4, respectively. Such variant DNA sequences may result from silent mutations (e.g., occurring during PCR amplification), or may be the product of deliberate mutagenesis of a native sequence.

The invention provides equivalent isolated DNA sequences encoding biologically active LDCAM, selected from: (a) cDNA comprising the nucleotide sequence presented in SEQ ID NO:1 and SEQ ID NO:3; (b) DNA capable of hybridization to a DNA of (a) under moderately stringent conditions and that encodes biologically active LDCAM; and (c) DNA that is degenerate as a result of the genetic code to a DNA defined in (a), or (b) and that encodes biologically active LDCAM. LDCAM proteins encoded by such DNA equivalent sequences are encompassed by the invention.

DNAs that are equivalent to the DNA sequence of SEQ ID NO:1 and SEQ ID NO:3 will hybridize under moderately and severely stringent conditions to DNA sequences that encode polypeptides comprising SEQ ID NO:2, and SEQ ID NO:4. Examples of LDCAM proteins encoded by such DNA, include, but are not limited to, LDCAM fragments (including soluble fragments) and LDCAM proteins comprising inactivated N-glycosylation site(s), inactivated KEX2 protease processing site(s), or conservative amino acid substitution(s), as described above. LDCAM proteins encoded by DNA derived from other mammalian species, wherein the DNA will hybridize to the cDNA of SEQ ID NO:1 or SEQ ID NO:3 are also encompassed by the present invention.

Variants possessing the ability to bind B7L-1 may be identified by any suitable assay. Biological activity of LDCAM may be determined, for example, by competition for binding to the binding domain of B7L-1 (i.e. competitive binding assays).

One type of a competitive binding assay for a LDCAM polypeptide uses a radiolabeled, soluble LDCAM and intact cells expressing B7L-1-expressing. Instead of intact cells, one could substitute soluble B7L-1/Fc fusion proteins such as a B7L-1/Fc bound to a solid phase through the interaction of a Protein A, Protein G or an antibody to the B7L-1 or Fc portions of the molecule, with the Fc region of the fusion protein. Another type of competitive binding assay utilizes a radiolabeled soluble LDCAM receptor and intact cells expressing LDCAM.

Competitive binding assays can be performed following conventional methodology. For example, radiolabeled LDCAM can be used to compete with a putative LDCAM homologue to assay for binding activity against B7L-1 or a surface-bound LDCAM receptor. Qualitative results can be obtained by competitive autoradiographic plate binding assays, or Scatchard plots may be utilized to generate quantitative results.

Alternatively, LDCAM-binding proteins, such as B7L-1 and anti-LDCAM antibodies, can be bound to a solid phase such as a column chromatography matrix or a similar substrate suitable for identifying, separating or purifying cells that express LDCAM on their surface. Binding of a LDCAM-binding protein to a solid phase contacting surface can be accomplished by any means, for example, by constructing a B7L-1/Fc fusion protein and binding such to the solid phase through the interaction of Protein A or Protein G. Various other means for fixing proteins to a solid phase are well known in the art and are suitable for use in the present invention. For example, magnetic microspheres can be coated with B7L-1 and held in the incubation vessel through a magnetic field. Suspensions of cell mixtures containing LDCAM-expressing cells are contacted with the solid phase that has B7L-1 polypeptides thereon. Cells having LDCAM on their surface bind to the fixed B7L-1 and unbound cells then are washed away. This affinity-binding method is useful for purifying, screening or separating such LDCAM-expressing cells from solution. Methods of releasing positively selected cells from the solid phase are known in the art and encompass, for example, the use of enzymes. Such enzymes are preferably non-toxic and non-injurious to the cells and are preferably directed to cleaving the cell-surface binding partner. In the case of B7L-1:LDCAM interactions, the enzyme preferably frees the resulting cell suspension from the LDCAM material. The purified cell population, especially if obtained from fetal tissue, then may be used to repopulate mature (adult) tissues.

Alternatively, mixtures of cells suspected of containing LDCAM+ cells first can be incubated with biotinylated B7L-1. Incubation periods are typically at least one hour in duration to ensure sufficient binding to LDCAM The resulting mixture then is passed through a column packed with avidin-coated beads, whereby the high affinity of biotin for avidin provides the binding of the cell to the beads. Use of avidin-coated beads is known in the art. See Berenson, et al. *J. Cell. Biochem.,* 10D:239 (1986). Wash of unbound material and the release of the bound cells is performed using conventional methods.

As described above, B7L-1 can be used to separate cells expressing LDCAM, and,. In an alternative method, LDCAM or an extracellular domain or a fragment thereof can be conjugated to a detectable moiety such as $^{125}$I to detect B7L-1-expressing cells. Radiolabeling with $^{125}$I can be performed by any of several standard methodologies that yield a functional $^{125}$I-LDCAM molecule labeled to high specific activity. Or an iodinated or biotinylated antibody against the B7L-1 region or the Fc region of the molecule could be used. Another detectable moiety such as an enzyme that can catalyze a colorimetric or fluorometric reaction, biotin or avidin may be used. Cells to be tested for B7L-1-expression can be contacted with labeled LDCAM. After incubation, unbound labeled LDCAM is removed and binding is measured using the detectable moiety.

The binding characteristics of LDCAM (including variants) may also be determined using the conjugated, soluble LDCAM/Fc (for example, $^{125}$I-LDCAM/Fc) in competition assays similar to those described above. In this case, however, intact cells expressing LDCAM/Fc bound to a solid substrate, are used to measure the extent to which a sample containing a putative LDCAM variant competes for binding with a conjugated soluble binding partner for LDCAM.

Other means of assaying for LDCAM include the use of anti-LDCAM antibodies, cell lines that proliferate in response to LDCAM, or recombinant cell lines that proliferate in the presence of LDCAM.

The LDCAM proteins disclosed herein also may be employed to measure the biological activity of B7L-1 or other LDCAM binding proteins in terms of their binding affinity for LDCAM. As one example, LDCAM may be used in determining whether biological activity is retained after modification of B7L-1 (e.g., chemical modification, truncation, mutation, etc.). The biological activity of a B7L-1 protein thus can be ascertained before it is used in a research study, or possibly in the clinic, for example.

LDCAM proteins find use as reagents that may be employed by those conducting "quality assurance" studies, e.g., to monitor shelf life and stability of B7L-1 or other LDCAM binding protein under different conditions. To illustrate, LDCAM may be employed in a binding affinity study to measure the biological activity of an B7L-1 protein that has been stored at different temperatures, or produced in different cell types. The binding affinity of the modified B7L-1 protein for LDCAM is compared to that of an unmodified B7L-1 protein to detect any adverse impact of the modifications on biological activity of B7L-1. Likewise, the biological activity of a LDCAM protein can be assessed using B7L-1.

LDCAM polypeptides also find use as carriers for delivering agents attached thereto to T cells or other cells bearing B7L-1 or LDCAM. LDCAM proteins can be used to deliver diagnostic or therapeutic agents to these cells in in vitro or in vivo procedures. As described in Example 5, LDCAM is found on the PAE81BM cell line, which is an EBV transformed cell line. Thus, one example of such carrier use is to expose this cell line to a therapeutic agent/LDCAM conjugate to assess whether the agent exhibits cytotoxicity toward any EBV cancers. Additionally, since LDCAM is expressed on dendritic cells and CD40L activated B cells that are important in antigen presentation, LDCAM is a useful carrier for targeting, identifying, and purifying these cells. Also, LDCAM/diagnostic agent conjugates may be employed to detect the presence of dendritic cells and B cells in vitro or in vivo. Example 6 demonstrates that human LDCAM mRNA, transcripts are found in human breast, retinal, fetal liver, spleen, fetal heart, lung, placenta, thyroid and lung carcinoma. Similar studies for expression of mouse LDCAM mRNA showed that mouse LDCAM mRNA is found in whole embryo, testes, lymphoid derived dendritic cells and triple negative cells. Since, LDCAM binds to itself, LDCAM can be used to study its functional role in these tissues.

A number of different therapeutic agents or other functional markers attached to LDCAM may be used in conjugates in an assay to detect and compare the cytotoxic effects of the agents on the cells or study the role of LDCAM in tissues and cells. Diagnostic and therapeutic agents that may be attached to a LDCAM polypeptide include, but are not limited to, drugs, toxins, radionuclides, chromophores, enzymes that catalyze a colorimetric or fluorometric reaction, and the like, with the particular agent being chosen according to the intended application. Examples of drugs include those used in treating various forms of cancer, e.g., nitrogen mustards such as L-phenylalanine nitrogen mustard or cyclophosphamide, intercalating agents such as cis-diaminodichloro-platinum, antimetabolites such as 5-fluorouracil, vinca alkaloids such as vincristine, and antibiotics such as bleomycin, doxorubicin, daunorubicin, and derivatives thereof. Among the toxins are ricin, abrin, diptheria toxin, *Pseudomonas aeruginosa* exotoxin A, ribosomal inactivating proteins, mycotoxins such as trichothecenes, and derivatives and fragments (e.g., single chains) thereof. Radionuclides suitable for diagnostic use include, but are not limited to, $^{123}$I, $^{131}$I, $^{99m}$Tc, $^{111}$In, and $^{76}$Br. Radionuclides suitable for therapeutic use include, but are not limited to, $^{131}$I, $^{211}$At, $^{77}$Br, $^{186}$Re, $^{188}$Re, $^{212}$Pb, $^{212}$Bi, $^{109}$Pd, $^{64}$Cu, and $^{67}$Cu.

Such agents may be attached to the LDCAM by any suitable conventional procedure. LDCAM, being a protein, comprises functional groups on amino acid side chains that can be reacted with functional groups on a desired agent to form covalent bonds, for example. Alternatively, the protein or agent may be derivatized to generate or attach a desired reactive functional group. The derivatization may involve attachment of one of the bifunctional coupling reagents available for attaching various molecules to proteins (Pierce Chemical Company, Rockford, Ill.). A number of techniques for radiolabeling proteins are known. Radionuclide metals may be attached to LDCAM by using a suitable bifunctional chelating agent, for example.

Conjugates comprising LDCAM and a suitable diagnostic or therapeutic agent (preferably covalently linked) are thus prepared. The conjugates are administered or otherwise employed in an amount appropriate for the particular application.

As mentioned above, because LDCAM blocks T cell proliferation caused by ConA and PHA and does not inhibit TCR mAb induced T cell proliferation, the inhibitory effects of LDCAM on mitogen-induced T cell proliferation is likely due to the inhibition of cytokine secretion, e.g. IL-2. Accordingly, another use of the LDCAM of the present invention is as a research tool for studying the role that LDCAM plays in the production of IL-2 in T cells. The LDCAM polypeptides of the present invention also may be employed in in vitro assays for detection of B7L-1 or the interactions thereof.

One embodiment of the present invention is directed to a method of treating disorders associated with a malfunctioning immune system. More particularly, since LDCAM is known to block ConA stimulated T cells and PHA stimulated T cells, LDCAM may be useful in treating inflammation and autoimmune disorders mediated by T cell responses. A composition that includes a LDCAM protein, preferably a soluble polypeptide, and a pharmaceutically acceptable diluent or carrier may be administered to a mammal to treat such inflammation or autoimmune disorder.

SCID mice that have been injected with soluble LDCAM, in the form of LDCAM/Fc, experience an increase in splenic cellularity. Part of this increase is due to an increase in DX-5$^+$ cells, also known as natural killer cells (NK cells). When injected with LDCAM/Fc and IL-15, a NK cell growth factor, SCID mice demonstrate an increase in NK cells that is additive. This further evidences the ability of LDCAM, LDCAM fragments, and soluble LDCAM to generate NK cells. In view of this discovery, another embodiment of the present invention includes methods for increasing the number of NK cells in an individual by administering, to that individual, pharmaceutical compositions, of the present invention, containing LDCAM, soluble LDCAM, or LDCAM fragments. In another embodiment, NK cells may be increased ex vivo by contacting NK cells with LDCAM or soluble forms of LDCAM and allowing the NK cells to expand. Similarly, NK cells can be generated in vivo or ex vivo, as just described, by administering LDCAM or soluble forms of LDCAM in connection with additional cytokines or growth factors. Thus, the present methods for generating NK cells, in vivo or ex vivo can further include the use of an effective amount of a cytokine in sequential or concurrent combination with LDCAM. Such cytokines include, but are not limited to, interleukins ("ILs") IL-15, IL-3 and IL-4, a colony stimulating factor ("CSF") selected from the group consisting of granulocyte macrophage colony stimulating factor ("GM-CSF") or GM-CSF/IL-3 fusions, or other cytokines such as TNF-α, CD40 binding proteins (e.g. CD40-L), 4-1BB antagonists (e.g. antibodies immunoreactive with 4-1BB and 4-1BB-L) or c-kit ligand.

NK cells are large granular lymphocytes that are distinct from T or B lymphocytes in morphology and function. NK cells mediate killing certain tumor cells and virally infected cells in non-MHC restricted manners. Additionally, NK cells are involved in the rejection of donor cells by bone marrow transplant recipients. Since LDCAM increases NK cell numbers, LDCAM, soluble LDCAM, or LDCAM fragments are useful in combating virally infected cells and infectious diseases. Similarly, LDCAM, soluble LDCAM, and LDCAM fragments are useful for killing tumor cells. Accordingly, within the scope of the present invention are methods for treating infectious diseases and methods for treating individuals afflicted with tumors. Such therapeutic methods involve administering LDCAM, soluble forms of LDCAM, or LDCAM fragments to an individual in need of increasing their numbers of NK cells in order to kill tumor cells or enhance their ability to combat infectious disease. Similarly, the therapeutic methods of the present invention can be carried out by administering LDCAM, soluble LDCAM, e.g. LDCAM fusion protein, or LDCAM fragments sequentially or concurrently in combination cytokines. Such cytokines include, but are not limited to, interleukins ("ILs") IL-15, IL-3 and IL-4, a colony stimulating factor ("CSF") selected from the group consisting of granulocyte macrophage colony stimulating factor ("GM-CSF") or GM-CSF/IL-3 fusions, or other cytokines such as TNF-α, CD40 binding proteins (e.g. CD40-L), 4-1BB antagonists (e.g. antibodies immunoreactive with 4-1BB and 4-1BB-L) or c-kit ligand.

Further within the scope of the present invention are methods for preventing or decreasing the effect of organ and bone marrow transplant rejection by recipients of the transplant. Such methods involve treating recipients with a composition that includes a LDCAM inhibitor, thus inhibiting increases in NK cell populations and decreasing the ability of NK cells to reject transplants.

Treatment of human endothelial cells (aortic and umbilical cord) with a soluble form of human LDCAM results in calcium fluxes within the cells. Calcium fluxes in endothelial cells are important in modulating vascular permeability, endothelial cell migration and angiogenesis, and adhesion and transmigration of leukocytes. LDCAM polypeptides and LDCAM inhibitors may therefore be used to improve drug delivery across the blood-brain barrier, to augment an immune response against a tumor or pathogen, to lessen an autoimmune or inflammatory syndrome, to lessen leukocyte adhesion and formation of atherosclerotic plaques, to block angiogenesis, and in the treatment of pathogenic vascular leakage.

LDCAM polypeptides of the invention can be formulated according to known methods used to prepare pharmaceutically useful compositions. LDCAM can be combined in admixture, either as the sole active material or with other known active materials, with pharmaceutically suitable diluents (e.g., Tris-HCl, acetate, phosphate), preservatives (e.g., Thimerosal, benzyl alcohol, parabens), emulsifiers, solubilizers, adjuvants and/or carriers. Suitable carriers and their formulations are described in Remington's Pharmaceutical Sciences, 16th ed. 1980, Mack Publishing Co. In addition, such compositions can contain LDCAM complexed with polyethylene glycol (PEG), metal ions, or incorporated into polymeric compounds such as polyacetic acid, polyglycolic acid, hydrogels, etc., or incorporated into liposomes, microemulsions, micelles, unilamellar or multilamellar vesicles, erythrocyte ghosts or spheroblasts. Such compositions will influence the physical state, solubility, stability, rate of in vivo release, and rate of in vivo clearance of LDCAM. LDCAM can also be conjugated to antibodies against tissue-specific receptors, ligands or antigens, or coupled to ligands of tissue-specific receptors. Where a LDCAM binding protein is found on tumor cells, the LDCAM may be conjugated to a toxin whereby LDCAM is used to deliver the toxin to the specific site, or may be used to sensitize such tumor cells to subsequently administered agents.

LDCAM can be administered topically, parenterally, or by inhalation. The term "parenteral" includes subcutaneous injections, intravenous, intramuscular, intracistemal injection, or infusion techniques. These compositions will typically contain an effective amount of the LDCAM, alone or in combination with an effective amount of any other active material. Such dosages and desired drug concentrations contained in the compositions may vary depending upon many factors, including the intended use, patient's body weight and age, and route of administration. Preliminary doses can be determined according to animal tests, and the scaling of dosages for human administration can be performed according to art-accepted practices.

LDCAM polypeptides may exist as oligomers, such as covalently linked or non-covalently-linked dimers or trimers. Oligomers may be linked by disulfide bonds formed between cysteine residues on different LDCAM polypeptides. In one embodiment of the invention, a LDCAM dimer is created by fusing LDCAM to the Fc region of an antibody (e.g., IgG1) in a manner that does not interfere with binding of LDCAM to the T cells, B7L-1 or itself. The Fc polypeptide preferably is fused to the C-terminus of a soluble LDCAM (comprising only the receptor binding). General preparation of fusion proteins comprising heterologous polypeptides fused to various portions of antibody-derived polypeptides (including the Fc domain) has been described, e.g., by Ashkenazi et al. (*PNAS USA* 88:10535, 1991) and Byrn et al. (*Nature* 344:677, 1990), hereby incorporated by reference. A gene fusion encoding the LDCAM:Fc fusion protein is inserted into an appropriate expression vector. LDCAM:Fc fusion proteins are allowed to assemble much like antibody molecules, whereupon interchain disulfide bonds form between Fc polypeptides, yielding divalent LDCAM. If fusion proteins are made with both heavy and light chains of an antibody, it is possible to form a LDCAM oligomer with as many as four LDCAM extracellular regions. Alternatively, one can link two soluble LDCAM domains with a peptide linker.

Suitable host cells for expression of LDCAM polypeptides include prokaryotes, yeast or higher eukaryotic cells. Appropriate cloning and expression vectors for use with bacterial, fungal, yeast, and mammalian cellular hosts are described, for example, in Pouwels et al. *Cloning Vectors: A Laboratory Manual*, Elsevier, N.Y., (1985). Cell-free translation systems could also be employed to produce LDCAM polypeptides using RNAs derived from DNA constructs disclosed herein.

Prokaryotes include gram negative or gram positive organisms, for example, *E. coli* or *Bacilli*. Suitable prokaryotic host cells for transformation include, for example, *E. coli, Bacillus subtilis, Salmonella typhimurium*, and various other species within the genera *Pseudomonas, Streptomyces*, and *Staphylococcus*. In a prokaryotic host cell, such as *E. coli*, a LDCAM polypeptide may include an N-terminal methionine residue to facilitate expression of the recombinant polypeptide in the prokaryotic host cell. The N-terminal Met may be cleaved from the expressed recombinant LDCAM polypeptide.

LDCAM polypeptides may be expressed in yeast host cells, preferably from the *Saccharomyces* genus (e.g., *S. cerevisiae*). Other genera of yeast, such as *Pichia , K. lactis* or *Kluyveromyces*, may also be employed. Yeast vectors will often contain an origin of replication sequence from a 2μ yeast plasmid, an autonomously replicating sequence (ARS), a promoter region, sequences for polyadenylation, sequences for transcription termination, and a selectable marker gene. Suitable promoter sequences for yeast vectors include, among others, promoters for metallothionein, 3-phosphoglycerate kinase (Hitzeman et al., *J. Biol. Chem.* 255:2073, 1980) or other glycolytic enzymes (Hess et al., *J. Adv. Enzyme Reg.* 7:149, 1968; and Holland et al., *Biochem.* 17:4900, 1978), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Other suitable vectors and promoters for use in yeast expression are further described in Hitzeman, EPA-73,657 or in Fleer et. al., *Gene*, 107:285-195 (1991); and van den Berg et. al., *Bio/Technology*, 8:135-139 (1990). Another alternative is the glucose-repressible ADH2 promoter described by Russell et al. (*J. Biol. Chem.* 258:2674, 1982) and Beier et al. (*Nature* 300:724, 1982). Shuttle vectors replicable in both yeast and *E. coli* may be constructed by inserting DNA sequences from pBR322 for selection and replication in *E. coli* (Amp$^r$ gene and origin of replication) into the above-described yeast vectors.

The yeast α-factor leader sequence may be employed to direct secretion of the LDCAM polypeptide. The α-factor leader sequence is often inserted between the promoter sequence and the structural gene sequence. See, e.g., Kurjan et al., *Cell* 30:933, 1982; Bitter et al., *Proc. Natl. Acad. Sci. USA* 81:5330, 1984; U.S. Pat. No. 4,546,082; and EP 324,274. Other leader sequences suitable for facilitating secretion of recombinant polypeptides from yeast hosts are known to those of skill in the art. A leader sequence may be modified near its 3' end to contain one or more restriction sites. This will facilitate fusion of the leader sequence to the structural gene.

Yeast transformation protocols are known to those of skill in the art. One such protocol is described by Hinnen et al., *Proc. Natl. Acad. Sci. USA* 75:1929, 1978. The Hinnen et al. protocol selects for Trp$^+$ transformants in a selective medium, wherein the selective medium consists of 0.67% yeast nitrogen base, 0.5% casamino acids, 2% glucose, 10 μg/ml adenine and 20 μg/ml uracil.

Yeast host cells transformed by vectors containing ADH2 promoter sequence may be grown for inducing expression in a "rich" medium. An example of a rich medium is one consisting of 1% yeast extract, 2% peptone, and 1% glucose supplemented with 80 μg/ml adenine and 80 μg/ml uracil. Derepression of the ADH2 promoter occurs when glucose is exhausted from the medium.

Mammalian or insect host cell culture systems could also be employed to express recombinant LDCAM polypeptides. Baculovirus systems for production of heterologous proteins in insect cells are reviewed by Luckow and Summers, *Bio/Technology* 6:47 (1988). Established cell lines of mammalian origin also may be employed. Examples of suitable mammalian host cell lines include the COS-7 line of monkey kidney cells (ATCC CRL 1651) (Gluzman et al., *Cell* 23:175, 1981), L cells, C127 cells, 3T3 cells (ATCC CCL 163), Chinese hamster ovary (CHO) cells, HeLa cells, and BHK (ATCC CRL 10) cell lines, and the CV-1/EBNA-1 cell line derived from the African green monkey kidney cell line CVI (ATCC CCL 70) as described by McMahan et al. (*EMBO J.* 10: 2821, 1991).

Transcriptional and translational control sequences for mammalian host cell expression vectors may be excised from viral genomes. Commonly used promoter sequences and enhancer sequences are derived from Polyoma virus, Adenovirus 2, Simian Virus 40 (SV40), and human cytomegalovirus. DNA sequences derived from the SV40 viral genome, for example, SV40 origin, early and late promoter, enhancer, splice, and polyadenylation sites may be used to provide other genetic elements for expression of a structural gene sequence in a mammalian host cell. Viral early and late promoters are particularly useful because both are easily obtained from a viral genome as a fragment which may also contain a viral origin of replication (Fiers et al., Nature 273:113, 1978). Smaller or larger SV40 fragments may also be used, provided the approximately 250 bp sequence extending from the Hind III site toward the Bgl I site located in the SV40 viral origin of replication site is included.

Exemplary expression vectors for use in mammalian host cells can be constructed as disclosed by Okayama and Berg (*Mol. Cell. Biol.* 3:280, 1983). A useful system for stable high level expression of mammalian cDNAs in C127 murine mammary epithelial cells can be constructed substantially as described by Cosman et al. (*Mol. Immunol.* 23:935, 1986). A useful high expression vector, PMLSV N1/N4, described by Cosman et al., Nature 312:768, 1984 has been deposited as ATCC 39890. Additional useful mammalian expression vectors are described in EP-A-0367566, and in U.S. patent application Ser. No. 07/701,415, filed May 16, 1991, incorporated by reference herein. The vectors may be derived from retroviruses. In place of the native signal sequence, and in addition to an initiator methionine, a heterologous signal sequence may be added, such as the signal sequence for IL-7 described in U.S. Pat. No. 4,965,195; the signal sequence for IL-2 receptor described in Cosman et al., Nature 312:768 (1984); the IL-4 signal peptide described in EP 367,566; the type I IL-1 receptor signal peptide described in U.S. Pat. No. 4,968,607; and the type II IL-1 receptor signal peptide described in EP 460,846.

LDCAM as an isolated, purified or homogeneous protein according to the invention may be produced by recombinant expression systems as described above or purified from naturally occurring cells. LDCAM can be purified to substantial homogeneity, as indicated by a single protein band upon analysis by SDS-polyacrylamide gel electrophoresis (SDS-PAGE).

One process for producing LDCAM comprises culturing a host cell transformed with an expression vector comprising a DNA sequence that encodes LDCAM under conditions sufficient to promote expression of LDCAM. LDCAM is then recovered from culture medium or cell extracts, depending upon the expression system employed. As is known to the skilled artisan, procedures for purifying a recombinant protein will vary according to such factors as the type of host cells employed and whether or not the recombinant protein is secreted into the culture medium.

For example, when expression systems that secrete the recombinant protein are employed, the culture medium first may be concentrated using a commercially available protein concentration filter, for example, an Amicon or Millipore Pellicon ultrafiltration unit. Following the concentration step, the concentrate can be applied to a purification matrix such as a gel filtration medium. Alternatively, an anion exchange resin can be employed, for example, a matrix or substrate having pendant diethylaminoethyl (DEAE) groups. The matrices can be acrylamide, agarose, dextran, cellulose or other types commonly employed in protein purification. Alternatively, a cation exchange step can be employed. Suitable cation exchangers include various insoluble matrices comprising sulfopropyl or carboxymethyl groups. Sulfopropyl groups are preferred. Finally, one or more reversed-phase high performance liquid chromatography (RP-HPLC) steps employing hydrophobic RP-HPLC media, (e.g., silica gel having pendant methyl or other aliphatic groups) can be employed to further purify LDCAM. Some or all of the foregoing purification steps, in various combinations, are well known and can be employed to provide a substantially homogeneous recombinant protein.

It is possible to utilize an affinity column comprising the ligand-binding domain of a LDCAM binding protein to affinity-purify expressed LDCAM polypeptides. LDCAM polypeptides can be removed from an affinity column using conventional techniques, e.g., in a high salt elution buffer and then dialyzed into a lower salt buffer for use or by changing pH or other components depending on the affinity matrix utilized. Alternatively, the affinity column may comprise an antibody that binds LDCAM. Example 10 describes a procedure for employing LDCAM of the invention to generate monoclonal antibodies directed against LDCAM.

Recombinant protein produced in bacterial culture can be isolated by initial disruption of the host cells, centrifugation, extraction from cell pellets if an insoluble polypeptide, or from the supernatant fluid if a soluble polypeptide, followed by one or more concentration, salting-out, ion exchange, affinity purification or size exclusion chromatography steps. Finally, RP-HPLC can be employed for final purification steps. Microbial cells can be disrupted by any convenient method, including freeze-thaw cycling, sonication, mechanical disruption, or use of cell lysing agents.

Transformed yeast host cells are preferably employed to express LDCAM as a secreted polypeptide in order to simplify purification. Secreted recombinant polypeptide from a yeast host cell fermentation can be purified by methods analogous to those disclosed by Urdal et al. (*J. Chromatog.* 296: 171, 1984). Urdal et al. describe two sequential, reversed-phase HPLC steps for purification of recombinant human IL-2 on a preparative HPLC column.

Useful fragments of the LDCAM nucleic acids include antisense or sense oligonucleotides comprising a single-stranded nucleic acid sequence (either RNA or DNA) capable of binding to target LDCAM mRNA (sense) or LDCAM DNA (antisense) sequences. Antisense or sense oligonucleotides, according to the present invention, comprise a fragment of the coding region of LDCAM cDNA. Such a fragment generally comprises at least about 14 nucleotides, preferably from about 14 to about 30 nucleotides. The ability to derive an antisense or a sense oligonucleotide, based upon a cDNA sequence encoding a given protein is described in, for example, Stein and Cohen (*Cancer Res.* 48:2659, 1988) and van der Krol et al. (*BioTechniques* 6:958, 1988).

Binding of antisense or sense oligonucleotides to target nucleic acid sequences results in the formation of duplexes that block transcription or translation of the target sequence by one of several means, including enhanced degradation of the duplexes, premature termination of transcription or translation, or by other means. The antisense oligonucleotides thus may be used to block expression of LDCAM proteins. Antisense or sense oligonucleotides further comprise oligonucleotides having modified sugar-phosphodiester backbones (or other sugar linkages, such as those described in WO91/06629) and wherein such sugar linkages are resistant to endogenous nucleases. Such oligonucleotides with resistant sugar linkages are stable in vivo (i.e., capable of resisting enzymatic degradation) but retain sequence specificity to be able to bind to target nucleotide sequences. Other examples of sense or antisense oligonucleotides include those oligonucleotides which are covalently linked to organic moieties, such as those described in WO 90/10448, and other moieties that increases affinity of the oligonucleotide for a target nucleic acid sequence, such as poly-(L-lysine). Further still, intercalating agents, such as ellipticine, and alkylating agents or metal complexes may be attached to sense or antisense oligonucleotides to modify binding specificities of the antisense or sense oligonucleotide for the target nucleotide sequence.

Antisense or sense oligonucleotides may be introduced into a cell containing the target nucleic acid sequence by any gene transfer method, including, for example, $CaPO_4$-mediated DNA transfection, electroporation, or by using gene transfer vectors such as Epstein-Barr virus. Antisense or sense oligonucleotides are preferably introduced into a cell containing the target nucleic acid sequence by insertion of the antisense or sense oligonucleotide into a suitable retroviral vector, then contacting the cell with the retrovirus vector containing the inserted sequence, either in vivo or ex vivo. Suitable retroviral vectors include, but are not limited to, those derived from the murine retrovirus M-MuLV, N2 (a retrovirus derived from M-MuLV), or the double copy vectors designated DCT5A, DCT5B and DCT5C (see PCT Application US 90/02656).

Sense or antisense oligonucleotides also may be introduced into a cell containing the target nucleotide sequence by formation of a conjugate with a ligand binding molecule, as described in WO 91/04753. Suitable ligand binding molecules include, but are not limited to, cell surface receptors, growth factors, other cytokines, or other ligands that bind to cell surface receptors. Preferably, conjugation of the ligand binding molecule does not substantially interfere with the ability of the ligand binding molecule to bind to its corresponding molecule or receptor, or block entry of the sense or antisense oligonucleotide or its conjugated version into the cell. Alternatively, a sense or an antisense oligonucleotide may be introduced into a cell containing the target nucleic acid sequence by formation of an oligonucleotide-lipid complex, as described in WO 90/10448. The sense or antisense oligonucleotide-lipid complex is preferably dissociated within the cell by an endogenous lipase.

In addition to the above, the following examples are provided to illustrate particular embodiments and not to limit the scope of the invention.

EXAMPLE 1

Preparing B7L-1/Fc Fusion Protein

The following describes generating a human B7L-1/Fc protein which was used to identify cells to which B7L-1 binds. The fusion protein includes the soluble extracellular region of human B7L-1 and the mutein human Fc region and was prepared by first isolating cDNA encoding the extracellular region of human B7L-1 using primers which flank the extracellular region of B7L-1 (See U.S. Pat. No. 5,011,912).

To isolate the nucleotides that encode the extracellular domain of B7L-1 (nucleotides 108-1249 of SEQ ID NO:1 of copending application Ser. No. 60/095,663 filed Aug. 7, 1998) oligonucleotides that flank the extracellular region of B7L-1 were used as primers in a PCR reaction to obtain a PCR product from clone #44904 which was the template in the reaction. The resulting PCR product was digested with Sal1 and Bg1II restriction enzymes at the Sal1 and Bg1II sites incorporated by the primers. The resulting fragment was ligated into an expression vector (pDC409) containing the human IgG1 Fc region mutated to lower Fc receptor binding.

The resulting DNA construct was transfected into the monkey kidney cell lines CV-1/EBNA (with co-transfection of psv3neo). After 7 days of culture in medium containing 0.5% low immunoglobulin bovine serum, a solution of 0.2% azide was added to the supernatant and the supernatant was filtered through a 0.22 µm filter. Then approximately 1 L of culture supernatant was passed through a BioCad Protein A HPLC protein purification system using a 4.6×100 mm Protein A column (POROS 20A from PerSeptive Biosystems) at 10 mL/min. The Protein A column binds the Fc Portion of the fusion protein in the supernatant, immobilizing the fusion protein and allowing other components of the supernatant to pass through the column. The column was washed with 30 mL of PBS solution and bound fusion protein was eluted from the HPLC column with citric acid adjusted to pH 3.0. Eluted purified fusion protein was neutralized as it eluted using 1M HEPES solution at pH 7.4.

EXAMPLE 2

B7L-1 Binding Studies

The B7L-1/Fc fusion protein prepared as described in Example 1 was used to screen cell lines for B7L-1 binding using quantitative binding studies according to standard flow cytometry methodologies. For each cell line screened, the procedure involved incubating cells blocked with 2% FCS (fetal calf serum), 5% normal goat serum and 5% rabbit serum in PBS for 1 hour. Then the blocked cells were incubated with 5 µg/mL of B7L-1/Fc fusion protein in 2% FCS, 5% goat serum and 5% rabbit serum in PBS. Following the incubation the sample was washed 2 times with FACS buffer (2% FCS in PBS) and then treated with mouse anti human Fc/biotin (purchased from Jackson Research) and SAPE (streptavidin-phycoerythrin purchased from Molecular Probes). This treatment causes the antihuman Fc/biotin to bind to any bound B7L-1/Fc and the SAPE to bind to the anti-human Fc/biotin resulting in a fluorescent identifying label on B7L-1/Fc which is bound to cells. The cells were analyzed for any bound protein using fluorescent detection flow cytometry. The results indicated that human B7L-1 binds well to human lung epithelial line (WI-28), human B lymphoblastoid lines (Daudi and PAE8LBM1), human fresh tonsillar B cells, murine $CD8^+$ dendritic cells from spleens/lymph nodes of flt3-L treated animals and murine T cell lymphoma S49.1.

EXAMPLE 3

Screening WI-26 Expression Library for B7L-1 Counter Receptors

The following describes screening a expression cloning library with the B7L-1/Fc fusion protein prepared as described in Example 1. The expression library was prepared from the human cell line WI-26 using methods described in *Current Protocols In Molecular Biology*, Vol. 1, (1987). Using standard indirect-binding methods, transfected monolayers of CV1/EBNA cells were assayed by slide autoradiography for expression of a B7L-1 counter receptor using radio-iodinated B7L-1/Fc fusion protein. Positive slides showing cells expressing a counter receptor were identified and one pool containing approximately 2,000 individual clones was identified as potentially positive for binding the B7L-1/Fc fusion protein.

The pool was titered and plated and then scraped to provide pooled plasmid DNA for transfection into CV1/EBNA cells.

After screening the smaller pools, one pool contained clones that were positive for B7L-1 counter receptor as indicated by the presence of an expressed gene product capable of binding to B7L-1/Fc. The positive pool was titered and plated to obtain individual colonies. DNA was isolated from each potential candidate clone, retransfected and rescreened. The resulting positive clones contained a cDNA insert of 1535 nucleotides. The cDNA coding region of the B7L-1 counter receptor (LDCAM) corresponds to that disclosed SEQ ID NO:1. The amino acid sequence encoded by SEQ ID NO:1 is disclosed in SEQ ID NO: 2.

EXAMPLE 4

Expressing Human LDCAM

To following describes expressing full length membrane-bound human LDCAM in CV1/EBNA cells. A vector construct for expressing human LDCAM was prepared by ligating the coding region of SEQ ID NO:1 into a pDC409 expression vector. The expression vector was then transfected in CV1/EBNA cells and LDCAM was expressed using techniques described in McMahan et al., *EMBO J.* 10:2821,1991.

After the cells were shocked and incubated for several days, cells having membrane bound LDCAM were harvested, fixed in 1% paraformaldehyde, washed and used in their intact form.

To express a soluble form of LDCAM that includes the LDCAM extracellular region encoded by nucleotides 8 to 1130 of SEQ ID NO:1, a vector construct is prepared by ligating the extracellular coding region of SEQ ID NO:1 into a pDC409 expression vector. The vector is transfected in CV1/EBNA cells Following a 3 day incubation period in fresh medium, soluble LDCAM is recovered by collecting CV1/EBNA cell supernatants containing the soluble form and isolating LDCAM using HPLC techniques or affinity chromatography techniques.

EXAMPLE 5

LDCAM Binding Studies

In order to identify cell lines to which LDCAM binds, the LDCAM/Fc fusion protein, described in Example 9 below, was prepared and used in cell binding and FACS assays. Using standard cell binding and FACS methodologies, LDCAM was found to bind to the B lymphoblastoid cell lines, DAUDI and PAE8LBM1, cells transfected with human B7L-1, cells transfected with LDCAM, S49.1 cells, and to the lymphoid DCs from spleens and lymph nodes of Flt3-L treated mice.

EXAMPLE 6

Identifying Tissue Expressing LDCAM

Using standard RT-PCR methodologies, Northern analyses and EST data base (GENBANK) sequence matching, a number of cell lines were examined for mRNA expression of human LDCAM and mouse LDCAM. The results demonstrated that LDCAM has a widespread tissue distribution. Expression of human LDCAM was found in breast, retina, fetal liver, spleen, fetal heart, lung, muscle, placenta, thyroid, and lung carcinoma. Mouse mRNA LDCAM was found in whole embryo, testes, and triple negative cells.

EXAMPLE 7

Isolating Murine LDCAM

Since the soluble human B7L-1 demonstrated binding to the murine lymphoma S49.1 (Example 2), a S49.1 expression library was screened for murine LDCAM cDNA clones. The process involved RT-PCR methodologies using the S49.1 cell line RNA and primers described in SEQ ID NO:7 and SEQ ID NO:8. These primers are based on a murine EST, discovered in a database and having homology to human LDCAM. The cDNAs were amplified by PCR using the primers, confirming the murine LDCAM is present in S49.1 cells.

The amplified product was cloned into a cloning vector and clones containing a LDCAM cDNA insert were detected by hybridization with an oligonucleotide complementary to the human LDCAM coding region. To detect cDNAs with 5' extensions as compared with human LDCAM an oligonucleotide primer complementary to the 5' end of the coding region and a primer complementary to vector sequences adjacent to the cDNA insert were used to perform anchored PCR so that the 5' region of the cDNA clones is amplified. The PCR products were examined by gel electrophoresis and their lengths were compared with a similarly derived amplification product from the human LDCAM cDNA. The cDNA inserts for the clones giving longer 5' PCR product were sequenced to give a murine LDCAM cDNA encoding all but the first 4 amino acids, as compared with the human LDCAM. The nucleotide sequence for murine LDCAM is given in SEQ ID NO:3. The amino acid sequence encoded by the nucleotide sequence of SEQ ID NO:3 is provided in SEQ ID NO:4.

EXAMPLE 8

Expressing Murine LDCAM Polypeptide

To prepare a vector construct for expressing murine extracellular B7L-1 the coding region of SEQ ID NO:3 was ligated into a pDC409 expression vector. The expression vector was then transfected in CV1/EBNA cells and LDCAM was expressed using techniques described in McMahan et al., *EMBO J.* 10:2821,1991.

After the cells were shocked and incubated for several days, cell supernatants containing soluble murine LDCAM were collected and the protein was recovered using HPLC techniques.

EXAMPLE 9

Preparing LDCAM/Fusion Proteins

The following describes generating a human LDCAM/Fc protein which was used to identify cells to which LDCAM binds. The fusion protein includes the soluble extracellular region of human LDCAM and the mutein human Fc region and was prepared by first isolating cDNA encoding the extracellular region of human LDCAM using primers which flank the extracellular region of LDCAM (See U.S. Pat. No. 5,011,912).

To isolate the nucleotides that encode the extracellular domain of LDCAM, nucleotides 16-1137 of SEQ ID NO:1, oligonucleotides that flank the extracellular region of LDCAM were used as primers in a PCR reaction to obtain a PCR product from the WI-26 clone. The primers are shown in SEQ ID NO:5 and SEQ ID NO:6. The resulting PCR product was digested with Sal1 and Bg1II restriction enzymes at the Sal1 and Bg1II sites incorporated by the primers. The resulting fragment was ligated into an expression vector (pDC409) containing the human IgG1 Fc region mutated to lower Fc receptor binding.

The resulting DNA construct was transfected into the monkey kidney cell lines CV-1/EBNA. After 7 days of culture in medium containing 0.5% low immunoglobulin bovine serum, a solution of 0.2% azide was added to the supernatant and the supernatant was filtered through a 0.22 µm filter. Then approximately 1 L of culture supernatant was passed through a BioCad Protein A HPLC protein purification system using a 4.6×100 mm Protein A column (POROS 20A from PerSeptive Biosystems) at 10 mL/min. The Protein A column binds the Fc Portion of the fusion protein in the supernatant, immobilizing the fusion protein and allowing other components of the supernatant to pass through the column. The column was washed with 30 mL of PBS solution and bound fusion protein was eluted from the HPLC column with citric acid adjusted to pH 3.0. Eluted purified fusion protein was neutralized as it eluted using 1M HEPES solution at pH 7.4.

EXAMPLE 10

Monoclonal Antibodies to LDCAM

This example illustrates a method for preparing monoclonal antibodies to LDCAM. Purified LDCAM, a fragment thereof such as the extracellular domain, synthetic peptides or cells that express LDCAM can be used to generate monoclonal antibodies against LDCAM using conventional techniques, for example, those techniques described in U.S. Pat. No. 4,411,993. Briefly, mice are immunized with LDCAM as an immunogen emulsified in complete Freund's adjuvant, and injected in amounts ranging from 10-100 µg subcutaneously or intraperitoneally. Ten to twelve days later, the immunized animals are boosted with additional LDCAM emulsified in incomplete Freund's adjuvant. Mice are periodically boosted thereafter on a weekly to bi-weekly immunization schedule. Serum samples are periodically taken by retroorbital bleeding or tail-tip excision to test for LDCAM antibodies by dot blot assay or ELISA (Enzyme-Linked Immunosorbent Assay).

Following detection of an appropriate antibody titer, positive animals are provided one last intravenous injection of LDCAM in saline. Three to four days later, the animals are sacrificed, spleen cells harvested, and spleen cells are fused to a murine myeloma cell line, e.g., NS1 or preferably P3×63Ag8.653 (ATCC CRL 1580). Fusions generate hybridoma cells, which are plated in multiple microtiter plates in a HAT (hypoxanthine, aminopterin and thymidine) selective medium to inhibit proliferation of non-fused cells, myeloma hybrids, and spleen cell hybrids.

The hybridoma cells are screened by ELISA for reactivity against purified B7L-1 by adaptations of the techniques disclosed in Engvall et al., *Immunochem.* 8:871, 1971 and in U.S. Pat. No. 4,703,004. A preferred screening technique is the antibody capture technique described in Beckmann et al., (*J. Immunol.* 144:4212, 1990) Positive hybridoma cells can be injected intraperitoneally into syngeneic BALB/c mice to produce ascites containing high concentrations of anti-LDCAM monoclonal antibodies. Alternatively, hybridoma cells can be grown in vitro in flasks or roller bottles by various techniques. Monoclonal antibodies produced in mouse ascites can be purified by ammonium sulfate precipitation, followed by gel exclusion chromatography. Alternatively, affinity chromatography based upon binding of antibody to protein A or protein G can also be used, as can affinity chromatography based upon binding to B7L-1.

EXAMPLE 11

Detecting LDCAM Expression By Northern Blot Analyses

The following describes Northern Blot experiments carried out to identify tissue and cell types that express LDCAM polypeptides of the present invention.

Northern blots were generated by fractionating 5 µg to 10 µg of total RNA on a 1.2% agarose formaldehyde gel and blotting the RNA onto Hybond Nylon membranes (Amersham, Arlington Heights, Ill.). Standard northern blot generating procedures as described in Maniatis, (*Molecular Cloning: a Laboratory Manual*, Cold Spring Harbor Lab. Press, 1989) were used. Poly A+ multiple tissue blots containing 1 µg of mRNA from a number of different sources were purchased from Clonetech.

A riboprobe, containing the coding region of LDCAM, was generated using Promega's Riboprobe Combination Kit and T7 RNA Polymerase according to the manufacturer's instruction. The results of probing the Northern blots and visualizing the resulting x-ray film for positively binding probes show that a 5.0 kB hybridizing mRNA was detected for murine LDCAM in lung, liver, brain, testes and splenic dendritic cells. Additional hybridizing mRNA having different sizes included an approximately 1.9 kB mRNA in lung and testes; an approximately 3.0 kB mRNA in LPS stimulated bone marrow macrophages, lung and testes; an approximately 7.0 kB hybridizing mRNA in anti-T cell receptor antibody stimulated splenic T cells, LPS stimulated bone marrow macrophages, and testes; and, an approximately 9.0 kB hybridizing mRNA was detected in thymus and anti-T cell receptor antibody stimulated splenic T cells.

EXAMPLE 12

Immune System Cell Binding Studies

The following describes FACS cell binding experiments that demonstrate that LDCAM binds to certain activated immune system cells. For study and comparison purposes, the binding characteristics of B7L-1 are also included. Cells studied included murine T cells, human T cells, murine B cells, murine NK cells, human endothelial cells, and human tumor cell lines.

To study murine T cell binding, BALB/c murine lymph node (LN) cells were cultured in culture medium alone and in the presence of different stimuli for 18-20 hours. The cultured cells were harvested and prepared for binding studies using B7L1/Fc fusion protein, LDCAM/Fc fusion protein and a control Fc protein. Following an overnight culture BALB/c murine LN cells are typically >90% CD3+. Bound protein was detected using flow cytometric analysis. The results shown in Table I indicate observed binding expressed as mean fluorescence intensity units (MFI) on unstimulated T cells (medium) and on stimulated T cells (by stimuli).

TABLE I

| Fc | medium | Con A | TCR mAb | PHA |
|---|---|---|---|---|
| control Fc | 12.7 | 10.4 | 14.5 | 14.2 |
| B7L1Fc | 11.7 | 14.3 | 24.0 | 12.6 |
| LDCAM Fc | 18.7 | 51.7 | 230.0 | 91.4 |

When analyzed by T cell subsets, 75-80% of LN CD4+ murine T cells displayed detectable LDCAM binding after anti-TCR stimulation in vitro. About 50% of LN CD8+ murine T cells display detectable binding. In addition, CD4+ T cells exhibit higher levels of LDCAM binding than do CD8+ murine T cells. The results demonstrate that LDCAM/Fc binds at low levels to naive T cells. However, after an overnight activation with polyclonal stimuli binding increased 5-20 fold depending on the stimuli. Of the stimuli studied PMA induces the least LDCAM binding to murine T cells, and anti-TCR induces the highest binding.

To study human T cells binding to LDCAM and it counterstructure B7L1, human peripheral blood (PB) T cells were cultured in culture medium only or in the presence of different stimuli for 18-20 hours. The cultured cells were harvested and prepared for binding studies using either B7L/1Fc fusion protein, LDCAM/Fc fusion protein and a control Fc protein. Bound protein on the human PB T cells was determined by flow cytometric analysis. Table II details results observed, expressed as MFI, on unstimulated T cells (medium) and on stimulated T cells( by stimuli).

TABLE II

| Fc | medium | Con A | PMA | PHA |
|---|---|---|---|---|
| control Fc | 4.7 | 4.8 | 3.5 | 4.3 |
| B7L1Fc | 6.3 | 7.5 | 4.5 | 5.7 |
| LDCAM Fc | 22.3 | 42.8 | 61.9 | 38.8 |

The results show that, PMA induces greater LDCAM binding on human T cells than it does on murine T cells. The presence of specific binding of LDCAM to both murine and human T cells in the absence of B7L1 binding suggests that LDCAM is binding to B7L1, or a different molecule and not to itself. Because studies indicate that T cells express little or no B7L1, LDCAM may have another binding partner.

Studies similar to those described above were performed to evaluate LDCAM and B7L1 binding to murine splenic B cells. Neither B7L1 nor LDCAM binding was detected on unstimulated murine B cells. Culturing murine splenic B cells with muCD40L or LPS induced low levels of LDCAM binding but no appreciable level of B7L1 binding was detected.

In order to study binding to murine NK cells, spleens were removed from IL-15 treated CB-17/SCID mice and used as a source for highly enriched and activated murine NK cells. Spleen cells isolated from IL-15 treated SCID mice are 60-80% DX-5 positive. DX-5 is a pan NK marker than is expressed on NK cells from many different strains of mice. Flow cytometric analysis was performed as described above to detect B7L1 and LDCAM binding to DX-5+ in vivo IL-15 activated murine NK cells. Table II gives the results of a binding murine NK cell binding study.

TABLE III

| Fc molecule | DX-5+ NK cell %+/MFI |
|---|---|
| control Fc | 8%/88 |
| B7L1Fc | 19%/265 |
| LDCAM Fc | 38%/432 |

In contrast to that which was observed on murine and human T cells, LDCAM and B7L1 binding can be detected on in vivo activated murine NK cells.

Results of experiments directed at studying B7L1 and LDCAM binding to human endothelial cells demonstrated no binding on human umbilical vein endothelial cells (HUVEC) from different donors. However, one HUVEC from one donor B7L1 did induce low levels of CD62E and CD106 compared to control Fc.

Table IV details the results of experiments directed at evaluating B7L1 and LDCAM binding to human tumor cell lines. The results are expressed as percentage of cells binding LDCAM or B7L1.

TABLE IV

| Cell line | Cell type | LDCAMFc (%+)** | B7L1Fc (%+)** |
|---|---|---|---|
| U937 | monocytic leukemia | 10 | 7 |
| K562 | erythroblastic leukemia | 7 | 5 |
| Jurkat | acute T cell leukemia | 10 | 7 |
| MP-1 | B-cell LCL | 46 | 10 |
| DAUDI-hi | B-cell Burkitt's | 8 | 6 |
| RPMI 8866 | B-cell lymphoma | 0 | 0 |
| #88EBV | B-cell LCL | 4 | 3 |
| #33EBV | B-cell LCL | 0 | 0 |
| Tonsil G EBV | B-cell LCL | 25 | 13 |
| MDA231 | breast adenocarcinoma | 8 | 9 |
| OVCAR-3 | ovarian carcinoma | 48 | 30 |
| H2126M1 | lung adenocarcinoma | 0 | 0 |

**binding of control Fc has been subtracted out so this is net %+ cells binding over background The results show significant LDCAM binding on ovarian carcinoma cell line and 2 of the human B-cell tumor lines (MP-1 and Tonsil G). B7L1 also binds to these three tumor cell lines but a much lower levels. These results demonstrate that LDCAM is a marker for certain types of B cell lymphomas or different types of carcinomas. In addition, biological signaling mediated by LDCAM or B7L1 could mediate functional anti tumor effects on these types of tumors.

EXAMPLE 13

Effects of LDCAM on T Cell Proliferation

The following discussion describes experiments performed to evaluate the effects of LDCAM on murine and human T cell proliferation induced by polyclonal stimuli.

LDCAM/Fc fusion protein and B7L1/Fc fusion protein were evaluated in a standard model of in vitro murine T cell proliferation. Lymph node (LN) cells were obtained from normal BALB/c mice and placed in culture in media. Varying amounts of control Fc, B7L1/Fc and LDCAM/Fc alone or in the presence of different polyclonal stimuli for T cells including ConA, PHA or immobilized TCR mAb were placed in the culture media.

The results of these experiments demonstrated that LDCAM strongly inhibits ConA induced murine T cell proliferation (50% inhibition at ~0.625 ug/ml), moderately inhibits PHA induced proliferation ( 50% inhibition at ~5 ug/ml) and does not effect the proliferation induced by immobilized TCR mAb. In human peripheral blood T cell proliferation assays, LDCAM inhibits ConA induced proliferation but does not effectively inhibit PHA or OKT3-induced proliferation. B7L1/Fc does not effect the proliferative responses of murine or human T cells.

Results suggest that the inhibitory effects of LDCAM/Fc on mitogen-induced murine and human T cell proliferation are due to inhibition of cytokine secretion (especially IL-2) or due to regulation of downstream responses of the T cell following activation and increases in the expression of the LDCAM binding partner. LDCAM may also modulate cell to cell interactions between T cells, T cells and APC or T cells and NK cells. The inability of LDCAM to inhibit TCR mAb induced proliferation suggests that cytokine dysregulation is occurring in that proliferation induced by ConA and PHA is very cytokine dependent where as that induced by anti TCR mAb is less so.

EXAMPLE 14

Effects of LDCAM on Murine T Cell Cytokine Production

The following describes experiments performed in order to evaluate LDCAM for its effects on murine LN cell or purified T cell cytokine secretion following the in vivo activation of T cells with PHA, ConA and TCR mAb. Results are shown in Table V. The levels of cytokine detected are expressed in pg/ml.

TABLE V

| culture condition | Fc molecule | IL-2(pg/ml) | IFN-gamma(pg/ml) |
|---|---|---|---|
| media | none | <2 | <10 |
|  | control Fc | <2 | <10 |
|  | LDCAM/Fc | <2 | <10 |
| ConA | none | 366 | 100 |
|  | control Fc | 614 | 244 |
|  | LDCAM/Fc | <2 | <10 |
| PHA | none | 36 | 358 |
|  | control Fc | 39 | 354 |
|  | LDCAM/Fc | 10 | <10 |
| immob. TCR mAb | none | 1703 | 1114 |
|  | control Fc | 1722 | 1215 |
|  | LDCAM/Fc | 1642 | 1027 |

The results show that LDCAM/Fc significantly inhibits murine LN T cell IL-2 and IFN-gamma production that is induced by both ConA and PHA. When immobilized anti TCR mAb is used to induce cytokine production from murine T cell, less pronounced effects of LDCAM on cytokine production were observed. LDCAM decreased IFN-gamma production after TCR activation. In contrast, IL-2 production was not decreased after TCR activation. Very little IL-4 was generated by the T cells in these experiments so whether or not LDCAM effects T cell production of IL-4 or other additional cytokines/chemokines was not evaluated.

EXAMPLE 15

Effects of LDCAM on Murine Mixed Cell Activation Assays

An in vitro mixed cell assay was developed to examine the ability of T cells to activate B cells through their CD40L/CD40 interaction. The assay involves culturing spleen cells and LN cells with anti-TCR mAb in vitro for 36 hours followed by the flow cytometric analysis T and B cell/APC cell activation that occurs after T cells become activated and interact with B cells/APCs.

Spleen cells were cultured with anti TCR mAb, ConA, PHA or in media only with control Fc or LDCAM/Fc for 36 hours. CD19+ B cell and CD3+ T cell activation was followed by examining cell surface expression of CD25, CD69, CD54, CD45Rb, CD44, CD28, CD23, CD86 and CD152 using two-color staining and flow cytometric analysis.

The results demonstrated that after activation with PHA or ConA the expression of CD69, CD54, and CD25 increases several fold on T cells and B cells in the culture. Compared to a control Fc which has little effect on these increases, LDCAM significantly reduced expression (almost to the same levels as non-activated T cells) of CD69, CD54 and CD25 that are induced on both cells types in this culture system via activation with ConA. The ConA activates the T cells which express activation molecules (e.g. CD40L) on their surface. The activation molecules bind to receptors on the surface of B cells and activate the B cells to express various activation-related proteins on their cell surface. The inhibition PHA activated T and B cells occurred to a more moderate extent to that observed after activation with ConA.

In addition, LDCAM decreased the levels of CD45RB expressed on both CD3+ and CD3− in spleen cells cultured with ConA. This effect on decreasing CD45RB levels was more pronounced when LDCAM was cultured with spleen cells stimulated with TCR mAb and was not observed when PHA was used as a stimulus or when the cells were cultured in medium alone.

Using TCR mAb to stimulate the cultured spleen cells in the presence of a control Fc or LDCAM/Fc showed that the levels of CD69, CD25, and CD25 induced on T cells and B cells by this stimulus were not effected by LDCAM. However, LDCAM increased the expression of CD28 on both CD3+ T cells and non-T cells. In one experiment the increase was 5-10 fold and in the other experiments the increase was 50%. This was also observed in one experiment when ConA was used as a stimulus in addition to TCR mAb. LDCAM caused moderate decreases in the intensity of CD45RB expression on B cells (50% decrease) and T cells (20-30% decrease) after activation with TCR mAb.

Interestingly, LDCAM does not effect CD45RB expression on spleen cells when they are cultured in the absence of polyclonal T cell stimuli. CD45RB expression in rodents has been reported to decrease as T cells progress from naive to memory cells. Also different subpopulations of CD4+ T cells express high or low levels of CD45RB and mediate distinct immune functions in vivo.

The above discussed results suggest that under certain immune stimulation conditions, particularly stimulations by ConA and PHA, LDCAM inhibits T cell activation at the cellular level in mixed cell assays and inhibits T cell proliferation induced by these mitogens at least partially by decreasing IL-2 and IFN-gamma production.

While LDCAM modestly down-regulates IFN gamma production induced by TCR mAb-induced activation, it has little effect on IL-2 production in this system and does not effect proliferation of murine T cells induced by immobilized TCR mAb. LDCAM does cause an increase in the TCR mAb activated T-cell and B-cell expression of CD28 and a decrease in CD45RB expression. Based on these data, LDCAM or its binding partner on T cells can regulate (increase, decrease or redirect) T cell effector-dependent immune responses in vivo including but not limited to anti-tumor immune responses, DTH responses, and T-cell dependent anti-infectious disease immune responses.

The above results suggest that LDCAM is useful in modulating T cell activation pathways and can be used to treat autoimmune diseases and inflammation.

EXAMPLE 16

LDCAM.Fc Binds to Murine NK Cells and Causes NK Cell Expansion

The following describes experiments that demonstrate that LDCAM binds to the surface of splenic NK cells constitutively and that activation of these cells with IL-15 increased the levels of LDCAM binding. The experiments also describes administering LDCAM:Fc to CB-17 SCID mice and the effects of the administration on NK cell expansion and activation in the spleen.

Twelve age-matched female CB-17/SCID mice were divided into 4 groups, with 3 animals per group. On day O, day 1 and day 2, group I, group II, group III and group IV were administered the following proteins IP: group I mice received 10 μg of human IgG; group II mice received 10 μg of human IL-15; group III mice received 10 μg of human LDCAM:Fc (lot# 7488-16 from Immunex); and, group IV received 10 μg each of human LDCAM:Fc and human IL-15.

On day 3 (the 4$^{th}$ day of the experiment), the mice were euthanized and their spleens were removed. Each spleen was enumerated separately and then pooled together for flow cytometric analysis. The number of NK cells in the spleen of each treated group was determined by flow cytometry using the DX-5 antibody as a pan-murine NK cell marker. In addition, other measures of NK cell activation including CD69 and CD54 expression were evaluated.

The results for the experiment are shown in Table VI. Administration of LDCAM:Fc alone (Group III) increased the total recovered spleen cell number by about 5-fold over the human IgG control group (Group I). Administration of human IL-15 alone, (Group II) increased the total recovered spleen cell number by about 9-fold over the control group (Group I). Combination treatment with IL-15 and LDCAM increased the spleen cell number additively.

The number of NK cells recovered from the spleens correlated with the total cell recovery in the spleen. More particularly, LDCAM induced about a 5-fold increase in recovered NK cells; IL-15 caused about a 9-fold increase in recovered NK cells; and, the combination of LDCAM and IL-15 induced about a 13-fold increase in the number of NK cells recovered from the spleens of treated mice. LDCAM also increased the number of NK cells in the spleen that expressed CD69 and CD54. This increase was due to overall NK cell expansion rather than specific increases in the expression of CD69 or CD54 on NK cells in vivo following LDCAM:Fc administration.

TABLE VI

| SCID Mice Group | spleen cell counts × $10^6$ | Number of Mice | % DX-5$^+$ cells (NK) | # of NK cells recovered × $10^6$ |
|---|---|---|---|---|
| Group I (human IgG control) | 2.3 | 3 | 67.8 | 1.6 |
| Group II (IL15 positive control) | 17.8 | 3 | 81.7 | 14.5 |
| Group III (LDCAM:Fc) | 10.25 | 3 | 51.2 | 5.3 |
| LDCAM:Fc and IL15 | 24.8 | 3 | 72.6 | 18.0 |

What is claimed is:

1. An isolated antibody that specifically binds to SEQ ID NO:2.

2. The antibody of claim 1, wherein the antibody is a monoclonal antibody.

3. The antibody of claim 1, wherein the antibody specifically binds to the extracellular domain of SEQ ID NO:2, wherein the extracellular domain comprises amino acids 39 to 374 of SEQ ID NO:2.

4. The antibody of claim 3, wherein the antibody is a monoclonal antibody.

5. A hybridoma that produces the antibody of claim 4.

* * * * *

SEQUENCE LISTING

```
<160> NUMBER OF SEQ ID NOS: 10

<210> SEQ ID NO 1
<211> LENGTH: 1598
<212> TYPE: DNA
<213> ORGANISM: homo sapiens
<220> FEATURE:
<221> NAME/KEY: CDS
<222> LOCATION: (16)..(1341)
<223> OTHER INFORMATION:

<400> SEQUENCE: 1
gcggccgcgc ccgac atg gcg agt gta gtg ctg ccg agc gga tcc cag tgt       51
                Met Ala Ser Val Val Leu Pro Ser Gly Ser Gln Cys
                  1               5                  10 gcg gcg gca gcg gcg gcg gcg gcg cct ccc ggg ctc cgg ctc cgg ctt       99
Ala Ala Ala Ala Ala Ala Ala Ala Pro Pro Gly Leu Arg Leu Arg Leu
             15                  20                  25 ctg ctg ttg ctc ttc tcc gcc gcg gca ctg atc ccc aca ggt gat ggg      147
Leu Leu Leu Leu Phe Ser Ala Ala Ala Leu Ile Pro Thr Gly Asp Gly
         30                  35                  40 cag aat ctg ttt acg aaa gac gtg aca gtg atc gag gga gag gtt gcg      195
Gln Asn Leu Phe Thr Lys Asp Val Thr Val Ile Glu Gly Glu Val Ala
 45                  50                  55                  60 acc atc agt tgc caa gtc aat aag agt gac gac tct gtg att cag cta      243
Thr Ile Ser Cys Gln Val Asn Lys Ser Asp Asp Ser Val Ile Gln Leu
                 65                  70                  75 ctg aat ccc aac agg cag acc att tat ttc agg gac ttc agg cct ttg      291
Leu Asn Pro Asn Arg Gln Thr Ile Tyr Phe Arg Asp Phe Arg Pro Leu
             80                  85                  90 aag gac agc agg ttt cag ttg ctg aat ttt tct agc agt gaa ctc aaa      339
Lys Asp Ser Arg Phe Gln Leu Leu Asn Phe Ser Ser Ser Glu Leu Lys
         95                 100                 105
```

-continued

| | |
|---|---|
| gta tca ttg aca aac gtc tca att tct gat gaa gga aga tac ttt tgc<br>Val Ser Leu Thr Asn Val Ser Ile Ser Asp Glu Gly Arg Tyr Phe Cys<br>110                            115                     120 | 387 |
| cag ctc tat acc gat ccc cca cag gaa agt tac acc acc atc aca gtc<br>Gln Leu Tyr Thr Asp Pro Pro Gln Glu Ser Tyr Thr Thr Ile Thr Val<br>125                       130                       135                 140 | 435 |
| ctg gtc cca cca cgt aat ctg atg atc gat atc cag aaa gac act gcg<br>Leu Val Pro Pro Arg Asn Leu Met Ile Asp Ile Gln Lys Asp Thr Ala<br>                    145                     150                    155 | 483 |
| gtg gaa ggt gag gag att gaa gtc aac tgc act gct atg gcc agc aag<br>Val Glu Gly Glu Glu Ile Glu Val Asn Cys Thr Ala Met Ala Ser Lys<br>160                            165                     170 | 531 |
| cca gcc acg act atc agg tgg ttc aaa ggg aac aca gag cta aaa ggc<br>Pro Ala Thr Thr Ile Arg Trp Phe Lys Gly Asn Thr Glu Leu Lys Gly<br>          175                     180                    185 | 579 |
| aaa tcg gag gtg gaa gag tgg tca gac atg tac act gtg acc agt cag<br>Lys Ser Glu Val Glu Glu Trp Ser Asp Met Tyr Thr Val Thr Ser Gln<br>190                            195                     200 | 627 |
| ctg atg ctg aag gtg cac aag gag gac gat ggg gtc cca gtg atc tgc<br>Leu Met Leu Lys Val His Lys Glu Asp Asp Gly Val Pro Val Ile Cys<br>205                          210                              220 | 675 |
| cag gtg gag cac cct gcg gtc act gga aac ctg cag acc cag cgg tat<br>Gln Val Glu His Pro Ala Val Thr Gly Asn Leu Gln Thr Gln Arg Tyr<br>                    225                     230                    235 | 723 |
| cta gaa gta cag tat aag cct caa gtg cac att cag atg act tat cct<br>Leu Glu Val Gln Tyr Lys Pro Gln Val His Ile Gln Met Thr Tyr Pro<br>240                            245                     250 | 771 |
| cta caa ggc tta acc cgg gaa ggg gac gcg ctt gag tta aca tgt gaa<br>Leu Gln Gly Leu Thr Arg Glu Gly Asp Ala Leu Glu Leu Thr Cys Glu<br>                    255                     260                    265 | 819 |
| gcc atc ggg aag ccc cag cct gtg atg gta act tgg gtg aga gtc gat<br>Ala Ile Gly Lys Pro Gln Pro Val Met Val Thr Trp Val Arg Val Asp<br>270                            275                     280 | 867 |
| gat gaa atg cct caa cac gcc gta ctg tct ggg ccc aac ctg ttc atc<br>Asp Glu Met Pro Gln His Ala Val Leu Ser Gly Pro Asn Leu Phe Ile<br>285                          290                     295                 300 | 915 |
| aat aac cta aac aaa aca gat aat ggt aca tac cgc tgt gaa gct tca<br>Asn Asn Leu Asn Lys Thr Asp Asn Gly Thr Tyr Arg Cys Glu Ala Ser<br>                    305                     310                    315 | 963 |
| aac ata gtg ggg aaa gct cac tcg gat tat atg ctg tat gta tac gat<br>Asn Ile Val Gly Lys Ala His Ser Asp Tyr Met Leu Tyr Val Tyr Asp<br>320                            325                     330 | 1011 |
| ccc ccc aca act atc cct cct ccc aca aca acc acc acc acc acc<br>Pro Pro Thr Thr Ile Pro Pro Pro Thr Thr Thr Thr Thr Thr Thr<br>335                           340                      345 | 1059 |
| acc acc acc acc acc atc ctt acc atc atc aca gat tcc cga gca ggt<br>Thr Thr Thr Thr Thr Ile Leu Thr Ile Ile Thr Asp Ser Arg Ala Gly<br>350                            355                     360 | 1107 |
| gaa gaa ggc tcg atc agg gca gtg gat cat gcc gtg atc ggt ggc gtc<br>Glu Glu Gly Ser Ile Arg Ala Val Asp His Ala Val Ile Gly Gly Val<br>365                            370                     375                 380 | 1155 |
| gtg gcg gtg gtg gtg ttc gcc atg ctg tgc ttg ctc atc att ctg ggg<br>Val Ala Val Val Val Phe Ala Met Leu Cys Leu Leu Ile Ile Leu Gly<br>                    385                     390                    395 | 1203 |
| cgc tat ttt gcc aga cat aaa ggt aca tac ttc act cat gaa gcc aaa<br>Arg Tyr Phe Ala Arg His Lys Gly Thr Tyr Phe Thr His Glu Ala Lys<br>400                            405                     410 | 1251 |
| gga gcc gat gac gca gca gac gca gac aca gct ata atc aat gca gaa<br>Gly Ala Asp Asp Ala Ala Asp Ala Asp Thr Ala Ile Ile Asn Ala Glu | 1299 |

-continued

```
                415                 420                 425
gga gga cag aac aac tcc gaa gaa aag aaa gag tac ttc atc           1341
Gly Gly Gln Asn Asn Ser Glu Glu Lys Lys Glu Tyr Phe Ile
        430                 435                 440 tagatcagcc tttttgtttc aatgaggtgt ccaactggcc ctatttagat gataaagaga 1401 cagtgatatt ggaacttgcg agaaattcgt gtgttttttt atgaatgggt ggaaaggtgt 1461 gagactggga aggcttggga tttgctgtgt aaaaaaaaaa aaaaaatgtt ctttggaaag 1521 aaaaaagcgg ccgctttctt attctatttc aacattcagc ttaatcataa tcctaaaatc 1581 atacatgcta tttccat                                                1598
```

<210> SEQ ID NO 2
<211> LENGTH: 442
<212> TYPE: PRT
<213> ORGANISM: homo sapiens

<400> SEQUENCE: 2

```
Met Ala Ser Val Val Leu Pro Ser Gly Ser Gln Cys Ala Ala Ala
1               5                   10                  15

Ala Ala Ala Ala Pro Pro Gly Leu Arg Leu Arg Leu Leu Leu Leu
            20                  25                  30

Phe Ser Ala Ala Ala Leu Ile Pro Thr Gly Asp Gly Gln Asn Leu Phe
            35                  40                  45

Thr Lys Asp Val Thr Val Ile Glu Gly Glu Val Ala Thr Ile Ser Cys
        50                  55                  60

Gln Val Asn Lys Ser Asp Asp Ser Val Ile Gln Leu Leu Asn Pro Asn
65                  70                  75                  80

Arg Gln Thr Ile Tyr Phe Arg Asp Phe Arg Pro Leu Lys Asp Ser Arg
                85                  90                  95

Phe Gln Leu Leu Asn Phe Ser Ser Ser Glu Leu Lys Val Ser Leu Thr
            100                 105                 110

Asn Val Ser Ile Ser Asp Glu Gly Arg Tyr Phe Cys Gln Leu Tyr Thr
            115                 120                 125

Asp Pro Pro Gln Glu Ser Tyr Thr Thr Ile Thr Val Leu Val Pro Pro
        130                 135                 140

Arg Asn Leu Met Ile Asp Ile Gln Lys Asp Thr Ala Val Glu Gly Glu
145                 150                 155                 160

Glu Ile Glu Val Asn Cys Thr Ala Met Ala Ser Lys Pro Ala Thr Thr
                165                 170                 175

Ile Arg Trp Phe Lys Gly Asn Thr Glu Leu Lys Gly Lys Ser Glu Val
            180                 185                 190

Glu Glu Trp Ser Asp Met Tyr Thr Val Thr Ser Gln Leu Met Leu Lys
            195                 200                 205

Val His Lys Glu Asp Asp Gly Val Pro Val Ile Cys Gln Val Glu His
        210                 215                 220

Pro Ala Val Thr Gly Asn Leu Gln Thr Gln Arg Tyr Leu Glu Val Gln
225                 230                 235                 240

Tyr Lys Pro Gln Val His Ile Gln Met Thr Tyr Pro Leu Gln Gly Leu
                245                 250                 255

Thr Arg Glu Gly Asp Ala Leu Glu Leu Thr Cys Glu Ala Ile Gly Lys
            260                 265                 270

Pro Gln Pro Val Met Val Thr Trp Val Arg Val Asp Asp Glu Met Pro
            275                 280                 285

Gln His Ala Val Leu Ser Gly Pro Asn Leu Phe Ile Asn Asn Leu Asn
```

```
                    290                 295                 300
Lys Thr Asp Asn Gly Thr Tyr Arg Cys Glu Ala Ser Asn Ile Val Gly
305                 310                 315                 320

Lys Ala His Ser Asp Tyr Met Leu Tyr Val Tyr Asp Pro Thr Thr
                325                 330                 335

Ile Pro Pro Thr Thr Thr Thr Thr Thr Thr Thr Thr Thr
            340                 345                 350

Thr Ile Leu Thr Ile Ile Thr Asp Ser Arg Ala Gly Glu Glu Gly Ser
            355                 360                 365

Ile Arg Ala Val Asp His Ala Val Ile Gly Gly Val Val Ala Val Val
370                 375                 380

Val Phe Ala Met Leu Cys Leu Leu Ile Ile Leu Gly Arg Tyr Phe Ala
385                 390                 395                 400

Arg His Lys Gly Thr Tyr Phe Thr His Glu Ala Lys Gly Ala Asp Asp
                405                 410                 415

Ala Ala Asp Ala Asp Thr Ala Ile Ile Asn Ala Glu Gly Gly Gln Asn
            420                 425                 430

Asn Ser Glu Glu Lys Lys Glu Tyr Phe Ile
            435                 440

<210> SEQ ID NO 3
<211> LENGTH: 1935
<212> TYPE: DNA
<213> ORGANISM: mus musculus
<220> FEATURE:
<221> NAME/KEY: CDS
<222> LOCATION: (2)..(1270)
<223> OTHER INFORMATION:

<400> SEQUENCE: 3 g gcg gcg cct cca ggg ctc cgg ctc cgg ctc ctg ctg ttg ctc ctt tcg      49
  Ala Ala Pro Pro Gly Leu Arg Leu Arg Leu Leu Leu Leu Leu Leu Ser
  1               5                   10                  15 gcc gcg gca ctg atc ccc aca ggt gat gga cag aat ctg ttt act aaa        97
Ala Ala Ala Leu Ile Pro Thr Gly Asp Gly Gln Asn Leu Phe Thr Lys
            20                  25                  30 gac gtg aca gtg att gaa gga gaa gtg gca acc atc agc tgc cag gtc        145
Asp Val Thr Val Ile Glu Gly Glu Val Ala Thr Ile Ser Cys Gln Val
        35                  40                  45 aat aag agt gac gac tca gtg atc cag ctc ctg aac ccc aac agg cag        193
Asn Lys Ser Asp Asp Ser Val Ile Gln Leu Leu Asn Pro Asn Arg Gln
50                  55                  60 acc att tac ttc agg gac ttc agg cct ttg aag gac agc agg ttt cag        241
Thr Ile Tyr Phe Arg Asp Phe Arg Pro Leu Lys Asp Ser Arg Phe Gln
65                  70                  75                  80 ctg ctg aat ttt tct agc agt gaa ctc aaa gtg tca ctg acg aat gtc        289
Leu Leu Asn Phe Ser Ser Ser Glu Leu Lys Val Ser Leu Thr Asn Val
                85                  90                  95 tca atc tcg gat gaa ggg aga tac ttc tgc cag ctc tac acg gac ccc        337
Ser Ile Ser Asp Glu Gly Arg Tyr Phe Cys Gln Leu Tyr Thr Asp Pro
            100                 105                 110 cca cag gag agt tac acc acc atc aca gtc ctg gtt cct cca cgt aac        385
Pro Gln Glu Ser Tyr Thr Thr Ile Thr Val Leu Val Pro Pro Arg Asn
        115                 120                 125 ttg atg atc gat atc cag aaa gac acg gca gtt gaa ggg gag gag att        433
Leu Met Ile Asp Ile Gln Lys Asp Thr Ala Val Glu Gly Glu Glu Ile
130                 135                 140 gaa gtc aac tgt act gcc atg gcc agc aag cca gcg acg acc atc agg        481
Glu Val Asn Cys Thr Ala Met Ala Ser Lys Pro Ala Thr Thr Ile Arg
```

-continued

```
                  145                 150                 155                 160
tgg ttc aaa ggg aac aag gaa ctc aaa ggc aaa tca gag gtg gag gag       529
Trp Phe Lys Gly Asn Lys Glu Leu Lys Gly Lys Ser Glu Val Glu Glu
                165                 170                 175 tgg tcg gac atg tac act gtg acc agt cag ctg atg ctg aag gtg cac       577
Trp Ser Asp Met Tyr Thr Val Thr Ser Gln Leu Met Leu Lys Val His
            180                 185                 190 aag gag gac gac ggg gtc ccg gtg atc tgc cag gtg gag cac cct gcg       625
Lys Glu Asp Asp Gly Val Pro Val Ile Cys Gln Val Glu His Pro Ala
            195                 200                 205 gtc act gga aac ctg cag acc cag cgc tat cta gaa gtg cag tat aaa       673
Val Thr Gly Asn Leu Gln Thr Gln Arg Tyr Leu Glu Val Gln Tyr Lys
        210                 215                 220 ccg caa gtg cat atc cag atg act tac cct ctg caa ggc cta acc cgg       721
Pro Gln Val His Ile Gln Met Thr Tyr Pro Leu Gln Gly Leu Thr Arg
225                 230                 235                 240 gaa ggg gat gca ttt gag tta acg tgt gaa gcc atc ggg aag ccc cag       769
Glu Gly Asp Ala Phe Glu Leu Thr Cys Glu Ala Ile Gly Lys Pro Gln
                245                 250                 255 cct gtg atg gta act tgg gtg aga gtc gat gat gaa atg cct caa cat       817
Pro Val Met Val Thr Trp Val Arg Val Asp Asp Glu Met Pro Gln His
            260                 265                 270 gcc gta ctg tct ggg cca aac ctg ttc atc aat aac cta aac aaa aca       865
Ala Val Leu Ser Gly Pro Asn Leu Phe Ile Asn Asn Leu Asn Lys Thr
        275                 280                 285 gat aac ggt act tac cgc tgt gag gct tcc aac ata gtg gga aag gct       913
Asp Asn Gly Thr Tyr Arg Cys Glu Ala Ser Asn Ile Val Gly Lys Ala
        290                 295                 300 cat tcg gac tat atg ctg tat gta tac gat ccc ccc aca act atc cct       961
His Ser Asp Tyr Met Leu Tyr Val Tyr Asp Pro Pro Thr Thr Ile Pro
305                 310                 315                 320 cct ccc aca aca acc acc acc act acc acc acc acc acc acc atc         1009
Pro Pro Thr Thr Thr Thr Thr Thr Thr Thr Thr Thr Thr Thr Ile
                325                 330                 335 ctt acc atc atc aca gat tct cga gca ggt gaa gag ggg acc att ggg      1057
Leu Thr Ile Ile Thr Asp Ser Arg Ala Gly Glu Glu Gly Thr Ile Gly
            340                 345                 350 gca gtg gac cac gca gtg att ggt ggc gtc gta gcc gtg gtg gtg ttt      1105
Ala Val Asp His Ala Val Ile Gly Gly Val Val Ala Val Val Val Phe
        355                 360                 365 gcc atg cta tgc ttg ctc atc att ctg ggc cgc tat ttt gcc aga cat      1153
Ala Met Leu Cys Leu Leu Ile Ile Leu Gly Arg Tyr Phe Ala Arg His
        370                 375                 380 aaa ggt aca tac ttc act cat gaa gcc aaa gga gcc gat gac gca gca      1201
Lys Gly Thr Tyr Phe Thr His Glu Ala Lys Gly Ala Asp Asp Ala Ala
385                 390                 395                 400 gac gca gac aca gct ata atc aat gca gaa gga gga cag aac aac tcc      1249
Asp Ala Asp Thr Ala Ile Ile Asn Ala Glu Gly Gly Gln Asn Asn Ser
                405                 410                 415 gaa gaa aag aaa gag tac ttc atctagatca gccttttgt tccaatgagg          1300
Glu Glu Lys Lys Glu Tyr Phe
            420 tgtccaactg gcctgtttag atgataaaga gacagtgata ctggaacttt cgagaagctc   1360 gtgtggtttt tgttttgtt ttgttttttt atgagtgggt ggagagatgc gagactggga    1420 aggcttggga tttgcaatgt acaaacaaaa acaaagaatg ttctttgaaa gtacactctg   1480 ctgtttgaca cctctttta atctgggttt aatttgcttt gggttttggg tttttttggt    1540 tttttgtttt tttcatttat atttcttcct accaagtcaa acttgggtac ttggatttgg   1600
```

-continued

```
tttcggtaga ttgcagaaaa ttctgtgcct tgtttttcat tcgtttgttg tgtttcttcc    1660
ctcttgccca tttatttttc ccaaaatcaa atttgttttt ttccccctcc caaacctccc    1720 atttttttgga attgacctgc tggaattcct aagactttct ccctgttgcc agtttctttt   1780
atttgtgtta acggtgactg ctttctgttc caaattcagt ttcataaaag gaaaaccagc    1840
acaatttaga tttcatagtt cagaatttag tgtctccatg atgcatcctt ctctgttgtt    1900
gtaaagattt gggtgaagaa aaaaaaaaaa aaaaa                                1935
```

<210> SEQ ID NO 4
<211> LENGTH: 423
<212> TYPE: PRT
<213> ORGANISM: mus musculus

<400> SEQUENCE: 4

| Ala | Ala | Pro | Pro | Gly | Leu | Arg | Leu | Arg | Leu | Leu | Leu | Leu | Leu | Leu | Ser |
|---|---|---|---|---|---|---|---|---|---|---|---|---|---|---|---|
| 1 | | | | 5 | | | | | 10 | | | | | 15 | |

| Ala | Ala | Ala | Leu | Ile | Pro | Thr | Gly | Asp | Gly | Gln | Asn | Leu | Phe | Thr | Lys |
|---|---|---|---|---|---|---|---|---|---|---|---|---|---|---|---|
| | | | 20 | | | | | 25 | | | | | 30 | | |

| Asp | Val | Thr | Val | Ile | Glu | Gly | Glu | Val | Ala | Thr | Ile | Ser | Cys | Gln | Val |
|---|---|---|---|---|---|---|---|---|---|---|---|---|---|---|---|
| | | | 35 | | | | | 40 | | | | | 45 | | |

| Asn | Lys | Ser | Asp | Asp | Ser | Val | Ile | Gln | Leu | Leu | Asn | Pro | Asn | Arg | Gln |
|---|---|---|---|---|---|---|---|---|---|---|---|---|---|---|---|
| | 50 | | | | | 55 | | | | | 60 | | | | |

| Thr | Ile | Tyr | Phe | Arg | Asp | Phe | Arg | Pro | Leu | Lys | Asp | Ser | Arg | Phe | Gln |
|---|---|---|---|---|---|---|---|---|---|---|---|---|---|---|---|
| 65 | | | | | 70 | | | | | 75 | | | | | 80 |

| Leu | Leu | Asn | Phe | Ser | Ser | Ser | Glu | Leu | Lys | Val | Ser | Leu | Thr | Asn | Val |
|---|---|---|---|---|---|---|---|---|---|---|---|---|---|---|---|
| | | | | 85 | | | | | 90 | | | | | 95 | |

| Ser | Ile | Ser | Asp | Glu | Gly | Arg | Tyr | Phe | Cys | Gln | Leu | Tyr | Thr | Asp | Pro |
|---|---|---|---|---|---|---|---|---|---|---|---|---|---|---|---|
| | | | 100 | | | | | 105 | | | | | 110 | | |

| Pro | Gln | Glu | Ser | Tyr | Thr | Thr | Ile | Thr | Val | Leu | Val | Pro | Pro | Arg | Asn |
|---|---|---|---|---|---|---|---|---|---|---|---|---|---|---|---|
| | | | 115 | | | | | 120 | | | | | 125 | | |

| Leu | Met | Ile | Asp | Ile | Gln | Lys | Asp | Thr | Ala | Val | Glu | Gly | Glu | Glu | Ile |
|---|---|---|---|---|---|---|---|---|---|---|---|---|---|---|---|
| | 130 | | | | | 135 | | | | | 140 | | | | |

| Glu | Val | Asn | Cys | Thr | Ala | Met | Ala | Ser | Lys | Pro | Ala | Thr | Thr | Ile | Arg |
|---|---|---|---|---|---|---|---|---|---|---|---|---|---|---|---|
| 145 | | | | | 150 | | | | | 155 | | | | | 160 |

| Trp | Phe | Lys | Gly | Asn | Lys | Glu | Leu | Lys | Gly | Lys | Ser | Glu | Val | Glu | Glu |
|---|---|---|---|---|---|---|---|---|---|---|---|---|---|---|---|
| | | | | 165 | | | | | 170 | | | | | 175 | |

| Trp | Ser | Asp | Met | Tyr | Thr | Val | Thr | Ser | Gln | Leu | Met | Leu | Lys | Val | His |
|---|---|---|---|---|---|---|---|---|---|---|---|---|---|---|---|
| | | | 180 | | | | | 185 | | | | | 190 | | |

| Lys | Glu | Asp | Asp | Gly | Val | Pro | Val | Ile | Cys | Gln | Val | Glu | His | Pro | Ala |
|---|---|---|---|---|---|---|---|---|---|---|---|---|---|---|---|
| | 195 | | | | | 200 | | | | | 205 | | | | |

| Val | Thr | Gly | Asn | Leu | Gln | Thr | Gln | Arg | Tyr | Leu | Glu | Val | Gln | Tyr | Lys |
|---|---|---|---|---|---|---|---|---|---|---|---|---|---|---|---|
| | 210 | | | | | 215 | | | | | 220 | | | | |

| Pro | Gln | Val | His | Ile | Gln | Met | Thr | Tyr | Pro | Leu | Gln | Gly | Leu | Thr | Arg |
|---|---|---|---|---|---|---|---|---|---|---|---|---|---|---|---|
| 225 | | | | | 230 | | | | | 235 | | | | | 240 |

| Glu | Gly | Asp | Ala | Phe | Glu | Leu | Thr | Cys | Glu | Ala | Ile | Gly | Lys | Pro | Gln |
|---|---|---|---|---|---|---|---|---|---|---|---|---|---|---|---|
| | | | | 245 | | | | | 250 | | | | | 255 | |

| Pro | Val | Met | Val | Thr | Trp | Val | Arg | Val | Asp | Asp | Glu | Met | Pro | Gln | His |
|---|---|---|---|---|---|---|---|---|---|---|---|---|---|---|---|
| | | | 260 | | | | | 265 | | | | | 270 | | |

| Ala | Val | Leu | Ser | Gly | Pro | Asn | Leu | Phe | Ile | Asn | Asn | Leu | Asn | Lys | Thr |
|---|---|---|---|---|---|---|---|---|---|---|---|---|---|---|---|
| | | | 275 | | | | | 280 | | | | | 285 | | |

| Asp | Asn | Gly | Thr | Tyr | Arg | Cys | Glu | Ala | Ser | Asn | Ile | Val | Gly | Lys | Ala |
|---|---|---|---|---|---|---|---|---|---|---|---|---|---|---|---|
| | 290 | | | | | 295 | | | | | 300 | | | | |

| His | Ser | Asp | Tyr | Met | Leu | Tyr | Val | Tyr | Asp | Pro | Pro | Thr | Thr | Ile | Pro |
|---|---|---|---|---|---|---|---|---|---|---|---|---|---|---|---|

```
305                 310                 315                 320
Pro Pro Thr Thr Thr Thr Thr Thr Thr Thr Thr Thr Thr Thr Thr Ile
                325                 330                 335

Leu Thr Ile Ile Thr Asp Ser Arg Ala Gly Glu Glu Gly Thr Ile Gly
            340                 345                 350

Ala Val Asp His Ala Val Ile Gly Gly Val Val Ala Val Val Val Phe
        355                 360                 365

Ala Met Leu Cys Leu Leu Ile Ile Leu Gly Arg Tyr Phe Ala Arg His
    370                 375                 380

Lys Gly Thr Tyr Phe Thr His Glu Ala Lys Gly Ala Asp Asp Ala Ala
385                 390                 395                 400

Asp Ala Asp Thr Ala Ile Ile Asn Ala Glu Gly Gly Gln Asn Asn Ser
            405                 410                 415

Glu Glu Lys Lys Glu Tyr Phe
            420

<210> SEQ ID NO 5
<211> LENGTH: 29
<212> TYPE: DNA
<213> ORGANISM: Artificial Sequence
<220> FEATURE:
<223> OTHER INFORMATION: Oligonucleotide primer

<400> SEQUENCE: 5
tatgtcgaca tggcgagtgt agtgctgcc                                    29

<210> SEQ ID NO 6
<211> LENGTH: 30
<212> TYPE: DNA
<213> ORGANISM: Artificial Sequence
<220> FEATURE:
<223> OTHER INFORMATION: Oligonucleotide primer

<400> SEQUENCE: 6
atatagatct atgatccact gccctgatcg                                   30

<210> SEQ ID NO 7
<211> LENGTH: 1820
<212> TYPE: DNA
<213> ORGANISM: homo sapiens
<220> FEATURE:
<221> NAME/KEY: CDS
<222> LOCATION: (157)..(1452)
<223> OTHER INFORMATION:

<400> SEQUENCE: 7
aagcttggca cgaggcggtc cccacctcgg ccccgggctc cgaagcggct cgggggcgcc      60
ctttcggtca acatcgtagt ccaccccctc cccatcccca gccccgggg attcaggctc      120 gccagcgccc agccagggag ccggccggga agcgcg atg ggg gcc cca gcc gcc       174
                                        Met Gly Ala Pro Ala Ala
                                          1               5 tcg ctc ctg ctc ctg ctc ctg ctg ttc gcc tgc tgc tgg gcg ccc ggc       222
Ser Leu Leu Leu Leu Leu Leu Leu Phe Ala Cys Cys Trp Ala Pro Gly
         10                  15                  20 ggg gcc aac ctc tcc cag gac ggc tac tgg cag gag cag gat ttg gag       270
Gly Ala Asn Leu Ser Gln Asp Gly Tyr Trp Gln Glu Gln Asp Leu Glu
     25                  30                  35 ctg gga act ctg gct cca ctc gac gag gcc atc agc tcc aca gtc tgg       318
Leu Gly Thr Leu Ala Pro Leu Asp Glu Ala Ile Ser Ser Thr Val Trp
 40                  45                  50
```

```
agc agc cct gac atg ctg gcc agt caa gac agc cag ccc tgg aca tct    366
Ser Ser Pro Asp Met Leu Ala Ser Gln Asp Ser Gln Pro Trp Thr Ser
 55          60                  65                  70 gat gaa aca gtg gtg gct ggt ggc acc gtg gtg ctc aag tgc caa gtg    414
Asp Glu Thr Val Val Ala Gly Gly Thr Val Val Leu Lys Cys Gln Val
             75                  80                  85 aaa gat cac gag gac tca tcc ctg caa tgg tct aac cct gct cag cag    462
Lys Asp His Glu Asp Ser Ser Leu Gln Trp Ser Asn Pro Ala Gln Gln
                 90                  95                 100 act ctc tac ttt ggg gag aag aga gcc ctt cga gat aat cga att cag    510
Thr Leu Tyr Phe Gly Glu Lys Arg Ala Leu Arg Asp Asn Arg Ile Gln
            105                 110                 115 ctg gtt acc tct acg ccc cac gag ctc agc atc agc atc agc aat gtg    558
Leu Val Thr Ser Thr Pro His Glu Leu Ser Ile Ser Ile Ser Asn Val
        120                 125                 130 gcc ctg gca gac gag ggc gag tac acc tgc tca atc ttc act atg cct    606
Ala Leu Ala Asp Glu Gly Glu Tyr Thr Cys Ser Ile Phe Thr Met Pro
135                 140                 145                 150 gtg cga act gcc aag tcc ctc gtc act gtg cta gga att cca cag aag    654
Val Arg Thr Ala Lys Ser Leu Val Thr Val Leu Gly Ile Pro Gln Lys
                155                 160                 165 ccc atc atc act ggt tat aaa tct tca tta cgg gaa aaa gac aca gcc    702
Pro Ile Ile Thr Gly Tyr Lys Ser Ser Leu Arg Glu Lys Asp Thr Ala
            170                 175                 180 acc cta aac tgt cag tct tct ggg agc aag cct gca gcc cgg ctc acc    750
Thr Leu Asn Cys Gln Ser Ser Gly Ser Lys Pro Ala Ala Arg Leu Thr
        185                 190                 195 tgg aga aag ggt gac caa gaa ctc cac gga gaa cca acc cgc ata cag    798
Trp Arg Lys Gly Asp Gln Glu Leu His Gly Glu Pro Thr Arg Ile Gln
200                 205                 210 gaa gat ccc aat ggt aaa acc ttc act gtc agc agc tcg gtg aca ttc    846
Glu Asp Pro Asn Gly Lys Thr Phe Thr Val Ser Ser Ser Val Thr Phe
215                 220                 225                 230 cag gtt acc cgg gag gat gat ggg gcg agc atc gtg tgc tct gtg aac    894
Gln Val Thr Arg Glu Asp Asp Gly Ala Ser Ile Val Cys Ser Val Asn
                235                 240                 245 cat gaa tct cta aag gga gct gac aga tcc acc tct caa cgc att gaa    942
His Glu Ser Leu Lys Gly Ala Asp Arg Ser Thr Ser Gln Arg Ile Glu
            250                 255                 260 gtt tta tac aca cca act gcg atg att agg cca gac cct ccc cat cct    990
Val Leu Tyr Thr Pro Thr Ala Met Ile Arg Pro Asp Pro Pro His Pro
        265                 270                 275 cgt gag ggc cag aag ctg ttg cta cac tgt gag ggt cgc ggc aat cca   1038
Arg Glu Gly Gln Lys Leu Leu Leu His Cys Glu Gly Arg Gly Asn Pro
280                 285                 290 gtc ccc cag cag tac cta tgg gag aag gag ggc agt gtg cca ccc ctg   1086
Val Pro Gln Gln Tyr Leu Trp Glu Lys Glu Gly Ser Val Pro Pro Leu
295                 300                 305                 310 aag atg acc cag gag agt gcc ctg atc ttc cct ttc ctc aac aag agt   1134
Lys Met Thr Gln Glu Ser Ala Leu Ile Phe Pro Phe Leu Asn Lys Ser
                315                 320                 325 gac agt ggc acc tac ggc tgc aca gcc acc agc aac atg ggc agc tac   1182
Asp Ser Gly Thr Tyr Gly Cys Thr Ala Thr Ser Asn Met Gly Ser Tyr
            330                 335                 340 aag gcc tac tac acc ctc aat gtt aat gac ccc agt ccg gtg ccc tcc   1230
Lys Ala Tyr Tyr Thr Leu Asn Val Asn Asp Pro Ser Pro Val Pro Ser
        345                 350                 355 tcc tcc agc acc tac cac gcc atc atc ggt ggg atc gtg gct ttc att   1278
Ser Ser Ser Thr Tyr His Ala Ile Ile Gly Gly Ile Val Ala Phe Ile
360                 365                 370
```

-continued

```
gtc ttc ctg ctg ctc atc atg ctc atc ttc ctt ggc cac tac ttg atc     1326
Val Phe Leu Leu Leu Ile Met Leu Ile Phe Leu Gly His Tyr Leu Ile
375                 380                 385                 390 cgg cac aaa gga acc tac ctg aca cat gag gca aaa ggc tcc gac gat     1374
Arg His Lys Gly Thr Tyr Leu Thr His Glu Ala Lys Gly Ser Asp Asp
            395                 400                 405 gct cca gac gcg gac acg gcc atc atc aat gca gaa ggc ggg cag tca     1422
Ala Pro Asp Ala Asp Thr Ala Ile Ile Asn Ala Glu Gly Gly Gln Ser
        410                 415                 420 gga ggg gac gac aag aag gaa tat ttc atc tagaggcgcc tgcccacttc       1472
Gly Gly Asp Asp Lys Lys Glu Tyr Phe Ile
    425                 430 ctgcgccccc caggggccct gtggggactg ctggggccgt caccaacccg gacttgtaca   1532
gagcaaccgc agggccgccc ctcccgcttg ctccccagcc cacccacccc cctgtacaga   1592
atgtctgctt tgggtgcggt tttgtactcg gtttggaatg gggagggagg agggcggggg   1652
gagggagggt tgccctcag cccttccgt ggcttctctg catttgggtt attattattt    1712
ttgtaacaat cccaaatcaa atctgtctcc aggctggaga ggcaggagcc ctggggtgag   1772
aaaagcaaaa aacaaacaaa aaaaaaaaaa aaaaattcct gcggccgc               1820
```

<210> SEQ ID NO 8
<211> LENGTH: 432
<212> TYPE: PRT
<213> ORGANISM: homo sapiens

<400> SEQUENCE: 8

```
Met Gly Ala Pro Ala Ala Ser Leu Leu Leu Leu Leu Leu Leu Phe Ala
1               5                   10                  15

Cys Cys Trp Ala Pro Gly Gly Ala Asn Leu Ser Gln Asp Gly Tyr Trp
            20                  25                  30

Gln Glu Gln Asp Leu Glu Leu Gly Thr Leu Ala Pro Leu Asp Glu Ala
        35                  40                  45

Ile Ser Ser Thr Val Trp Ser Ser Pro Asp Met Leu Ala Ser Gln Asp
    50                  55                  60

Ser Gln Pro Trp Thr Ser Asp Glu Thr Val Val Ala Gly Gly Thr Val
65                  70                  75                  80

Val Leu Lys Cys Gln Val Lys Asp His Glu Asp Ser Ser Leu Gln Trp
                85                  90                  95

Ser Asn Pro Ala Gln Gln Thr Leu Tyr Phe Gly Glu Lys Arg Ala Leu
            100                 105                 110

Arg Asp Asn Arg Ile Gln Leu Val Thr Ser Thr Pro His Glu Leu Ser
        115                 120                 125

Ile Ser Ile Ser Asn Val Ala Leu Ala Asp Glu Gly Glu Tyr Thr Cys
    130                 135                 140

Ser Ile Phe Thr Met Pro Val Arg Thr Ala Lys Ser Leu Val Thr Val
145                 150                 155                 160

Leu Gly Ile Pro Gln Lys Pro Ile Ile Thr Gly Tyr Lys Ser Ser Leu
                165                 170                 175

Arg Glu Lys Asp Thr Ala Thr Leu Asn Cys Gln Ser Ser Gly Ser Lys
            180                 185                 190

Pro Ala Ala Arg Leu Thr Trp Arg Lys Gly Asp Gln Glu Leu His Gly
        195                 200                 205

Glu Pro Thr Arg Ile Gln Glu Asp Pro Asn Gly Lys Thr Phe Thr Val
    210                 215                 220
```

```
Ser Ser Ser Val Thr Phe Gln Val Thr Arg Glu Asp Gly Ala Ser
225                 230                 235                 240

Ile Val Cys Ser Val Asn His Glu Ser Leu Lys Gly Ala Asp Arg Ser
                245                 250                 255

Thr Ser Gln Arg Ile Glu Val Leu Tyr Thr Pro Thr Ala Met Ile Arg
            260                 265                 270

Pro Asp Pro His Pro Arg Glu Gly Gln Lys Leu Leu Leu His Cys
        275                 280                 285

Glu Gly Arg Gly Asn Pro Val Pro Gln Gln Tyr Leu Trp Glu Lys Glu
    290                 295                 300

Gly Ser Val Pro Pro Leu Lys Met Thr Gln Glu Ser Ala Leu Ile Phe
305                 310                 315                 320

Pro Phe Leu Asn Lys Ser Asp Ser Gly Thr Tyr Gly Cys Thr Ala Thr
                325                 330                 335

Ser Asn Met Gly Ser Tyr Lys Ala Tyr Tyr Thr Leu Asn Val Asn Asp
            340                 345                 350

Pro Ser Pro Val Pro Ser Ser Ser Thr Tyr His Ala Ile Ile Gly
        355                 360                 365

Gly Ile Val Ala Phe Ile Val Phe Leu Leu Leu Ile Met Leu Ile Phe
    370                 375                 380

Leu Gly His Tyr Leu Ile Arg His Lys Gly Thr Tyr Leu Thr His Glu
385                 390                 395                 400

Ala Lys Gly Ser Asp Asp Ala Pro Asp Ala Asp Thr Ala Ile Ile Asn
                405                 410                 415

Ala Glu Gly Gly Gln Ser Gly Gly Asp Asp Lys Lys Glu Tyr Phe Ile
            420                 425                 430

<210> SEQ ID NO 9
<211> LENGTH: 1718
<212> TYPE: DNA
<213> ORGANISM: homo sapiens
<220> FEATURE:
<221> NAME/KEY: CDS
<222> LOCATION: (157)..(1350)
<223> OTHER INFORMATION:

<400> SEQUENCE: 9
aagcttggca cgaggcggtc cccacctcgg ccccgggctc cgaagcggct cggggggcgcc      60 ctttcggtca acatcgtagt ccaccccctc cccatcccca gccccgggg attcaggctc     120 gccagcgccc agccagggag ccggccggga agcgcg atg ggg gcc cca gcc gcc     174
                                        Met Gly Ala Pro Ala Ala
                                        1               5 tcg ctc ctg ctc ctg ctc ctg ctg ttc gcc tgc tgc tgg gcg ccc ggc      222
Ser Leu Leu Leu Leu Leu Leu Leu Phe Ala Cys Cys Trp Ala Pro Gly
        10                  15                  20 ggg gcc aac ctc tcc cag gac gac agc cag ccc tgg aca tct gat gaa      270
Gly Ala Asn Leu Ser Gln Asp Asp Ser Gln Pro Trp Thr Ser Asp Glu
    25                  30                  35 aca gtg gtg gct ggt ggc acc gtg gtg ctc aag tgc caa gtg aaa gat      318
Thr Val Val Ala Gly Gly Thr Val Val Leu Lys Cys Gln Val Lys Asp
40                  45                  50 cac gag gac tca tcc ctg caa tgg tct aac cct gct cag cag act ctc      366
His Glu Asp Ser Ser Leu Gln Trp Ser Asn Pro Ala Gln Gln Thr Leu
55                  60                  65                  70 tac ttt ggg gag aag aga gcc ctt cga gat aat cga att cag ctg gtt      414
Tyr Phe Gly Glu Lys Arg Ala Leu Arg Asp Asn Arg Ile Gln Leu Val
                75                  80                  85
```

```
                                                             -continued
acc tct acg ccc cac gag ctc agc atc agc atc agc aat gtg gcc ctg     462
Thr Ser Thr Pro His Glu Leu Ser Ile Ser Ile Ser Asn Val Ala Leu
         90                  95                 100 gca gac gag ggc gag tac acc tgc tca atc ttc act atg cct gtg cga     510
Ala Asp Glu Gly Glu Tyr Thr Cys Ser Ile Phe Thr Met Pro Val Arg
            105                 110                 115 act gcc aag tcc ctc gtc act gtg cta gga att cca cag aag ccc atc     558
Thr Ala Lys Ser Leu Val Thr Val Leu Gly Ile Pro Gln Lys Pro Ile
        120                 125                 130 atc act ggt tat aaa tct tca tta cgg gaa aaa gac aca gcc acc cta     606
Ile Thr Gly Tyr Lys Ser Ser Leu Arg Glu Lys Asp Thr Ala Thr Leu
135                 140                 145                 150 aac tgt cag tct tct ggg agc aag cct gca gcc cgg ctc acc tgg aga     654
Asn Cys Gln Ser Ser Gly Ser Lys Pro Ala Ala Arg Leu Thr Trp Arg
            155                 160                 165 aag ggt gac caa gaa ctc cac gga gaa cca acc cgc ata cag gaa gat     702
Lys Gly Asp Gln Glu Leu His Gly Glu Pro Thr Arg Ile Gln Glu Asp
        170                 175                 180 ccc aat ggt aaa acc ttc act gtc agc agc tcg gtg aca ttc cag gtt     750
Pro Asn Gly Lys Thr Phe Thr Val Ser Ser Ser Val Thr Phe Gln Val
    185                 190                 195 acc cgg gag gat gat ggg gcg agc atc gtg tgc tct gtg aac cat gaa     798
Thr Arg Glu Asp Asp Gly Ala Ser Ile Val Cys Ser Val Asn His Glu
200                 205                 210 tct cta aag gga gct gac aga tcc acc tct caa cgc att gaa gtt tta     846
Ser Leu Lys Gly Ala Asp Arg Ser Thr Ser Gln Arg Ile Glu Val Leu
215                 220                 225                 230 tac aca cca act gcg atg att agg cca gac cct ccc cat cct cgt gag     894
Tyr Thr Pro Thr Ala Met Ile Arg Pro Asp Pro Pro His Pro Arg Glu
            235                 240                 245 ggc cag aag ctg ttg cta cac tgt gag ggt cgc ggc aat cca gtc ccc     942
Gly Gln Lys Leu Leu Leu His Cys Glu Gly Arg Gly Asn Pro Val Pro
        250                 255                 260 cag cag tac cta tgg gag aag gag ggc agt gtg cca ccc ctg aag atg     990
Gln Gln Tyr Leu Trp Glu Lys Glu Gly Ser Val Pro Pro Leu Lys Met
    265                 270                 275 acc cag gag agt gcc ctg atc ttc cct ttc ctc aac aag agt gac agt    1038
Thr Gln Glu Ser Ala Leu Ile Phe Pro Phe Leu Asn Lys Ser Asp Ser
280                 285                 290 ggc acc tac ggc tgc aca gcc acc agc aac atg ggc agc tac aag gcc    1086
Gly Thr Tyr Gly Cys Thr Ala Thr Ser Asn Met Gly Ser Tyr Lys Ala
295                 300                 305                 310 tac tac acc ctc aat gtt aat gac ccc agt ccg gtg ccc tcc tcc tcc    1134
Tyr Tyr Thr Leu Asn Val Asn Asp Pro Ser Pro Val Pro Ser Ser Ser
            315                 320                 325 agc acc tac cac gcc atc atc ggt ggg atc gtg gct ttc att gtc ttc    1182
Ser Thr Tyr His Ala Ile Ile Gly Gly Ile Val Ala Phe Ile Val Phe
        330                 335                 340 ctg ctg ctc atc atg ctc atc ttc ctt ggc cac tac ttg atc cgg cac    1230
Leu Leu Leu Ile Met Leu Ile Phe Leu Gly His Tyr Leu Ile Arg His
    345                 350                 355 aaa gga acc tac ctg aca cat gag gca aaa ggc tcc gac gat gct cca    1278
Lys Gly Thr Tyr Leu Thr His Glu Ala Lys Gly Ser Asp Asp Ala Pro
360                 365                 370 gac gcg gac acg gcc atc atc aat gca gaa ggc ggg cag tca gga ggg    1326
Asp Ala Asp Thr Ala Ile Ile Asn Ala Glu Gly Gly Gln Ser Gly Gly
375                 380                 385                 390 gac gac aag aag gaa tat ttc atc tagaggcgcc tgcccacttc ctgcgccccc    1380
Asp Asp Lys Lys Glu Tyr Phe Ile
            395
```

```
cagggggccct gtggggactg ctggggccgt caccaacccg gacttgtaca gagcaaccgc    1440
agggccgccc ctcccgcttg ctccccagcc cacccacccc cctgtacaga atgtctgctt    1500
tgggtgcggt tttgtactcg gtttggaatg gggagggagg agggcggggg gaggggaggg    1560
ttgccctcag cccttttccgt ggcttctctg catttgggtt attattattt ttgtaacaat    1620
cccaaatcaa atctgtctcc aggctggaga ggcaggagcc ctggggtgag aaaagcaaaa    1680
aacaaacaaa aaaaaaaaaa aaaaattcct gcggccgc                            1718

<210> SEQ ID NO 10
<211> LENGTH: 398
<212> TYPE: PRT
<213> ORGANISM: homo sapiens

<400> SEQUENCE: 10
```

Met Gly Ala Pro Ala Ala Ser Leu Leu Leu Leu Leu Leu Phe Ala
1               5                   10                  15

Cys Cys Trp Ala Pro Gly Gly Ala Asn Leu Ser Gln Asp Asp Ser Gln
        20                  25                  30

Pro Trp Thr Ser Asp Glu Thr Val Val Ala Gly Gly Thr Val Val Leu
    35                  40                  45

Lys Cys Gln Val Lys Asp His Glu Asp Ser Ser Leu Gln Trp Ser Asn
50                  55                  60

Pro Ala Gln Gln Thr Leu Tyr Phe Gly Glu Lys Arg Ala Leu Arg Asp
65                  70                  75                  80

Asn Arg Ile Gln Leu Val Thr Ser Thr Pro His Glu Leu Ser Ile Ser
                85                  90                  95

Ile Ser Asn Val Ala Leu Ala Asp Glu Gly Glu Tyr Thr Cys Ser Ile
            100                 105                 110

Phe Thr Met Pro Val Arg Thr Ala Lys Ser Leu Val Thr Val Leu Gly
        115                 120                 125

Ile Pro Gln Lys Pro Ile Ile Thr Gly Tyr Lys Ser Ser Leu Arg Glu
    130                 135                 140

Lys Asp Thr Ala Thr Leu Asn Cys Gln Ser Ser Gly Ser Lys Pro Ala
145                 150                 155                 160

Ala Arg Leu Thr Trp Arg Lys Gly Asp Gln Glu Leu His Gly Glu Pro
                165                 170                 175

Thr Arg Ile Gln Glu Asp Pro Asn Gly Lys Thr Phe Thr Val Ser Ser
            180                 185                 190

Ser Val Thr Phe Gln Val Thr Arg Glu Asp Asp Gly Ala Ser Ile Val
        195                 200                 205

Cys Ser Val Asn His Glu Ser Leu Lys Gly Ala Asp Arg Ser Thr Ser
    210                 215                 220

Gln Arg Ile Glu Val Leu Tyr Thr Pro Thr Ala Met Ile Arg Pro Asp
225                 230                 235                 240

Pro Pro His Pro Arg Glu Gly Gln Lys Leu Leu His Cys Glu Gly
                245                 250                 255

Arg Gly Asn Pro Val Pro Gln Gln Tyr Leu Trp Glu Lys Glu Gly Ser
            260                 265                 270

Val Pro Pro Leu Lys Met Thr Gln Glu Ser Ala Leu Ile Phe Pro Phe
        275                 280                 285

Leu Asn Lys Ser Asp Ser Gly Thr Tyr Gly Cys Thr Ala Thr Ser Asn
    290                 295                 300

Met Gly Ser Tyr Lys Ala Tyr Tyr Thr Leu Asn Val Asn Asp Pro Ser

```
-continued
305                 310                 315                 320

Pro Val Pro Ser Ser Ser Ser Thr Tyr His Ala Ile Ile Gly Gly Ile
                325                 330                 335

Val Ala Phe Ile Val Phe Leu Leu Leu Ile Met Leu Ile Phe Leu Gly
                340                 345                 350

His Tyr Leu Ile Arg His Lys Gly Thr Tyr Leu Thr His Glu Ala Lys
            355                 360                 365

Gly Ser Asp Asp Ala Pro Asp Ala Asp Thr Ala Ile Ile Asn Ala Glu
        370                 375                 380

Gly Gly Gln Ser Gly Gly Asp Asp Lys Lys Glu Tyr Phe Ile
385                 390                 395
```